United States Patent
Palti

(10) Patent No.: US 7,805,201 B2
(45) Date of Patent: *Sep. 28, 2010

(54) TREATING A TUMOR OR THE LIKE WITH AN ELECTRIC FIELD

(75) Inventor: Yoram Palti, Haifa (IL)

(73) Assignee: Standen Ltd., St. Hellier, Jersey (*) Notice: Subject to any disclaimer, the term of this patent is extended or adjusted under 35 U.S.C. 154(b) by 1081 days.

This patent is subject to a terminal disclaimer.

(21) Appl. No.: 11/111,236

(22) Filed: Apr. 21, 2005

(65) Prior Publication Data

US 2005/0209640 A1 Sep. 22, 2005

Related U.S. Application Data

(63) Continuation-in-part of application No. 11/074,318, filed on Mar. 7, 2005, now Pat. No. 7,706,890, which is a continuation-in-part of application No. 10/315,576, filed on Dec. 10, 2002, now Pat. No. 6,868,289, which is a continuation-in-part of application No. 10/285,313, filed on Oct. 31, 2002, now Pat. No. 7,089,054, which is a continuation-in-part of application No. 10/263,329, filed on Oct. 2, 2002, now Pat. No. 7,136,699, which is a continuation-in-part of application No. 10/402,327, filed on Mar. 28, 2003, now Pat. No. 7,146,210, which is a continuation-in-part of application No. 10/204,334, filed as application No. PCT/IB01/00202 on Feb. 16, 2001, now Pat. No. 7,333,852, and a continuation-in-part of application No. 10/288,562, filed on Nov. 5, 2002, now Pat. No. 7,016,725.

(60) Provisional application No. 60/565,065, filed on Apr. 23, 2004, provisional application No. 60/183,295, filed on Feb. 17, 2000, provisional application No. 60/338,632, filed on Nov. 6, 2001.

(51) Int. Cl.
*A61N 1/00* (2006.01)

(52) U.S. Cl. .................................................. 607/76
(58) Field of Classification Search .................. 607/76, 607/2; 604/20, 114; 128/898
See application file for complete search history.

(56) References Cited

U.S. PATENT DOCUMENTS 2,220,269 A 11/1940 Patzold et al.

(Continued)

FOREIGN PATENT DOCUMENTS

EP 0 330 797 A2 9/1989

(Continued)

OTHER PUBLICATIONS

Hofmann et al.,"Electronic Genetic-Physical and Biological Aspects of Cellular Electomanipulation",IEEE Eng. in Med. and Biology Mag., Dec. 1986,p. 6-23,New York.

(Continued)

*Primary Examiner*—George Manuel
(74) *Attorney, Agent, or Firm*—Proskauer

(57) ABSTRACT

Cells that are in the late anaphase or telophase stages of cell division are vulnerable to damage by AC electric fields that have specific frequency and field strength characteristics. The selective destruction of rapidly dividing cells can therefore be accomplished by imposing an AC electric field in a target region for extended periods of time. Some of the cells that divide while the field is applied will be damaged, but the cells that do not divide will not be harmed. This selectively damages rapidly dividing cells like tumor cells, but does not harm normal cells that are not dividing. Since the vulnerability of the dividing cells is strongly related to the alignment between the long axis of the dividing cells and the lines of force of the electric field, improved results are obtained when the field is sequentially imposed in different directions.

20 Claims, 24 Drawing Sheets

U.S. PATENT DOCUMENTS

| | | | |
|---|---|---|---|
| 3,991,770 A | 11/1976 | LeVeen | |
| 4,016,886 A | 4/1977 | Doss et al. | |
| 4,121,592 A | 10/1978 | Whalley | |
| 4,263,920 A | 4/1981 | Tasto et al. | |
| 4,467,809 A | 8/1984 | Brighton | |
| 4,472,506 A | 9/1984 | Liburdy | |
| 4,622,952 A | 11/1986 | Gordon | |
| 4,626,506 A | 12/1986 | Zimmermann et al. | |
| 4,676,258 A | 6/1987 | Inokuchi et al. | |
| 4,822,470 A | 4/1989 | Chang | |
| 4,846,178 A | 7/1989 | Fuxue et al. | |
| 4,846,196 A | 7/1989 | Wiksell et al. | |
| 4,923,814 A | 5/1990 | Marshall | |
| 4,936,303 A | 6/1990 | Derwiler et al. | |
| 4,971,991 A | 11/1990 | Umemura et al. | |
| 5,099,756 A | 3/1992 | Franconi et al. | |
| 5,158,071 A | 10/1992 | Umemura et al. | |
| 5,236,410 A | 8/1993 | Granov et al. | |
| 5,269,304 A | 12/1993 | Matthews | |
| 5,312,513 A | 5/1994 | Costerton et al. | |
| 5,312,813 A | 5/1994 | Costerton et al. | |
| 5,386,837 A | 2/1995 | Sterzer | |
| 5,389,069 A | 2/1995 | Weaver | |
| 5,441,532 A | 8/1995 | Fenn | |
| 5,441,746 A | 8/1995 | Chagnon | |
| 5,468,223 A | 11/1995 | Mir | |
| 5,606,971 A | 3/1997 | Sarvazyn | |
| 5,674,267 A | 10/1997 | Mir et al. | |
| 5,683,366 A * | 11/1997 | Eggers et al. | 604/114 |
| 5,718,246 A | 2/1998 | Vona | |
| 5,807,257 A | 9/1998 | Bridges | |
| 5,964,726 A | 10/1999 | Korenstein et al. | |
| 5,976,092 A | 11/1999 | Chinn | |
| 5,984,882 A | 11/1999 | Rosenschein et al. | |
| 6,027,488 A | 2/2000 | Hofmann et al. | |
| 6,043,066 A | 3/2000 | Mangano et al. | |
| 6,055,453 A | 4/2000 | Hofmann et al. | |
| 6,068,650 A | 5/2000 | Hofmann et al. | |
| 6,096,020 A | 8/2000 | Hofmann et al. | |
| 6,319,901 B1 | 11/2001 | Bernard et al. | |
| 6,366,808 B1 | 4/2002 | Schroeppel et al. | |
| 6,413,255 B1 | 7/2002 | Stern | |
| 6,447,499 B2 | 9/2002 | Gray | |
| 6,856,839 B2 | 2/2005 | Litovitz | |
| 7,467,011 B2 * | 12/2008 | Palti | 607/2 |
| 2002/0193832 A1 | 12/2002 | Gray | |
| 2002/0193833 A1 | 12/2002 | Dimmer et al. | |
| 2003/0060856 A1 | 3/2003 | Chornenky et al. | |
| 2003/0191508 A1 | 10/2003 | Shloznlkov | |

FOREIGN PATENT DOCUMENTS

| | | |
|---|---|---|
| GB | 1 419 660 A1 | 12/1975 |
| GB | 2 026 322 A1 | 2/1980 |
| GB | 2 043 453 A1 | 10/1980 |
| WO | WO 01/60994 | 8/2001 |

OTHER PUBLICATIONS

Berg et al.,"Electric Field Effects on Biological Membranes:Electoincorporation and Electofusion",Ettore Maj Inter. Science, 1987,p. 135-166,vol. 32,Phys. Science,New York.

Kirson et al., "Disruption of Cancer Cell Replication by Alternating Electric Fields", Cancer Research 64, May 2004, p. 3288-3295, Haifa, Israel.

Asbury et al., "Trapping of DNA in Nonuniform Oscillating Electic Fields", Biophysical Journal, Feb. 1998, p. 1024-1030,vol. 74,Seattle,WA.

* cited by examiner

Cross Section of Isolect With
and Without a Protecting Net

TREATING A TUMOR OR THE LIKE WITH AN ELECTRIC FIELD

CROSS-REFERENCE TO RELATED APPLICATIONS

This application claims the benefit of U.S. provisional application 60/565,065, filed Apr. 23, 2004, which is hereby incorporated by reference in its entirety. This application is also a continuation-in-part of U.S. patent application Ser. No. 11/074,318, filed Mar. 7, 2005, which is a continuation-in-part of U.S. patent application Ser. No. 10/315,576, filed Dec. 10, 2002, which is a continuation-in-part of U.S. patent application Ser. No. 10/285,313, filed Oct. 31, 2002, which is a continuation-in-part application of U.S. patent application Ser. No. 10/263,329, filed Oct. 2, 2002, each of which is hereby incorporated by reference in its entirety. This application is also a continuation-in-part of U.S. patent application Ser. No. 10/402,327, filed Mar. 28, 2003, which is a continuation-in-part of U.S. patent application Ser. No. 10/204,334, filed Oct. 16, 2002, which is the U.S. national phase of PCT/IB01/00202, filed Feb. 16, 2001, which claims the benefit of U.S. provisional application 60/183,295, filed Feb. 17, 2000, each of which is hereby incorporated by reference in its entirety. This application is also a continuation-in-part of U.S. patent application Ser. No. 10/288,562, filed Nov. 5, 2002, which claims the benefit of U.S. provisional application 60/338,632, filed Nov. 6, 2001, each of which is hereby incorporated by reference in its entirety.

TECHNICAL FIELD

This invention concerns selective destruction of rapidly dividing cells in a localized area, and more particularly, selectively destroying dividing cells without destroying nearby non-dividing cells by applying an electric field with specific characteristics to a target area in a living patient.

BACKGROUND

All living organisms proliferate by cell division, including cell cultures, microorganisms (such as bacteria, mycoplasma, yeast, protozoa, and other single-celled organisms), fungi, algae, plant cells, etc. Dividing cells of organisms can be destroyed, or their proliferation controlled, by methods that are based on the sensitivity of the dividing cells of these organisms to certain agents. For example, certain antibiotics stop the multiplication process of bacteria.

The process of eukaryotic cell division is called "mitosis", which involves nice distinct phases (see Darnell et al., Molecular Cell Biology, New York: Scientific American Books, 1986, p. 149). During interphase, the cell replicates chromosomal DNA, which begins condensing in early prophase. At this point, centrioles (each cell contains 2) begin moving towards opposite poles of the cell. In middle prophase, each chromosome is composed of duplicate chromatids. Microtubular spindles radiate from regions adjacent to the centrioles, which are closer to their poles. By late prophase, the centrioles have reached the poles, and some spindle fibers extend to the center of the cell, while others extend from the poles to the chromatids. The cells then move into metaphase, when the chromosomes move toward the equator of the cell and align in the equatorial plane. Next is early anaphase, during which time daughter chromatids separate from each other at the equator by moving along the spindle fibers toward a centromere at opposite poles. The cell begins to elongate along the axis of the pole; the pole-to-pole spindles also elongate. Late anaphase occurs when the daughter chromosomes (as they are now called) each reach their respective opposite poles. At this point, cytokinesis begins as the cleavage furrow begins to form at the equator of the cell. In other words, late anaphase is the point at which pinching the cell membrane begins. During telophase, cytokinesis is nearly complete and spindles disappear. Only a relatively narrow membrane connection joins the two cytoplasms. Finally, the membranes separate fully, cytokinesis is complete and the cell returns to interphase.

In meiosis, the cell undergoes a second division, involving separation of sister chromosomes to opposite poles of the cell along spindle fibers, followed by formation of a cleavage furrow and cell division. However, this division is not preceded by chromosome replication, yielding a haploid germ cell. Bacteria also divide by chromosome replication, followed by cell separation. However, since the daughter chromosomes separate by attachment to membrane components; there is no visible apparatus that contributes to cell division as in eukaryotic cells.

It is well known that tumors, particularly malignant or cancerous tumors, grow uncontrollably compared to normal tissue. Such expedited growth enables tumors to occupy an ever-increasing space and to damage or destroy tissue adjacent thereto. Furthermore, certain cancers are characterized by an ability to transmit cancerous "seeds", including single cells or small cell clusters (metastases), to new locations where the metastatic cancer cells grow into additional tumors.

The rapid growth of tumors, in general, and malignant tumors in particular, as described above, is the result of relatively frequent cell division or multiplication of these cells compared to normal tissue cells. The distinguishably frequent cell division of cancer cells is the basis for the effectiveness of existing cancer treatments, e.g., irradiation therapy and the use of various chemo-therapeutic agents. Such treatments are based on the fact that cells undergoing division are more sensitive to radiation and chemotherapeutic agents than non-dividing cells. Because tumors cells divide much more frequently than normal cells, it is possible, to a certain extent, to selectively damage or destroy tumor cells by radiation therapy and/or chemotherapy. The actual sensitivity of cells to radiation, therapeutic agents, etc., is also dependent on specific characteristics of different types of normal or malignant cell types. Thus, unfortunately, the sensitivity of tumor cells is not sufficiently higher than that many types of normal tissues. This diminishes the ability to distinguish between tumor cells and normal cells, and therefore, existing cancer treatments typically cause significant damage to normal tissues, thus limiting the therapeutic effectiveness of such treatments. Furthermore, the inevitable damage to other tissue renders treatments very traumatic to the patients and, often, patients are unable to recover from a seemingly successful treatment. Also, certain types of tumors are not sensitive at all to existing methods of treatment.

There are also other methods for destroying cells that do not rely on radiation therapy or chemotherapy alone. For example, ultrasonic and electrical methods for destroying tumor cells can be used in addition to or instead of conventional treatments. Electric fields and currents have been used for medical purposes for many years. The most common is the generation of electric currents in human or animal body by application of an electric field by means of a pair of conductive electrodes between which a potential difference is maintained. These electric currents are used either to exert their specific effects, i.e., to stimulate excitable tissue, or to generate heat by flowing in the body since it acts as a resistor. Examples of the first type of application include the following: cardiac defibrillators, peripheral nerve and muscle stimulators, brain stimulators, etc. Currents are used for heating, for example, in devices for tumor ablation, ablation of malfunctioning cardiac or brain tissue, cauterization, relaxation of muscle rheumatic pain and other pain, etc.

Another use of electric fields for medical purposes involves the utilization of high frequency oscillating fields transmitted from a source that emits an electric wave, such as an RF wave or a microwave source that is directed at the part of the body that is of interest (i.e., target). In these instances, there is no electric energy conduction between the source and the body; but rather, the energy is transmitted to the body by radiation or induction. More specifically, the electric energy generated by the source reaches the vicinity of the body via a conductor and is transmitted from it through air or some other electric insulating material to the human body.

In a conventional electrical method, electrical current is delivered to a region of the target tissue using electrodes that are placed in contact with the body of the patient. The applied electrical current destroys substantially all cells in the vicinity of the target tissue. Thus, this type of electrical method does not discriminate between different types of cells within the target tissue and results in the destruction of both tumor cells and normal cells.

Electric fields that can be used in medical applications can thus be separated generally into two different modes. In the first mode, the electric fields are applied to the body or tissues by means of conducting electrodes. These electric fields can be separated into two types, namely (1) steady fields or fields that change at relatively slow rates, and alternating fields of low frequencies that induce corresponding electric currents in the body or tissues, and (2) high frequency alternating fields (above 1 MHz) applied to the body by means of the conducting electrodes. In the second mode, the electric fields are high frequency alternating fields applied to the body by means of insulated electrodes.

The first type of electric field is used, for example, to stimulate nerves and muscles, pace the heart, etc. In fact, such fields are used in nature to propagate signals in nerve and muscle fibers, central nervous system (CNS), heart, etc. The recording of such natural fields is the basis for the ECG, EEG, EMG, ERG, etc. The field strength in these applications, assuming a medium of homogenous electric properties, is simply the voltage applied to the stimulating/recording electrodes divided by the distance between them. These currents can be calculated by Ohm's law and can have dangerous stimulatory effects on the heart and CNS and can result in potentially harmful ion concentration changes. Also, if the currents are strong enough, they can cause excessive heating in the tissues. This heating can be calculated by the power dissipated in the tissue (the product of the voltage and the current).

When such electric fields and currents are alternating, their stimulatory power, on nerve, muscle, etc., is an inverse function of the frequency. At frequencies above 1-10 KHz, the stimulation power of the fields approaches zero. This limitation is due to the fact that excitation induced by electric stimulation is normally mediated by membrane potential changes, the rate of which is limited by the RC properties (time constants on the order of 1 ms) of the membrane.

Regardless of the frequency, when such current inducing fields are applied, they are associated with harmful side effects caused by currents. For example, one negative effect is the changes in ionic concentration in the various "compartments" within the system, and the harmful products of the electrolysis taking place at the electrodes, or the medium in which the tissues are imbedded. The changes in ion concentrations occur whenever the system includes two or more compartments between which the organism maintains ion concentration differences. For example, for most tissues, [$Ca^{++}$] in the extracellular fluid is about $2 \times 10^{-3}$ M, while in the cytoplasm of typical cells its concentration can be as low as $10^{-7}$ M. A current induced in such a system by a pair of electrodes, flows in part from the extracellular fluid into the cells and out again into the extracellular medium. About 2% of the current flowing into the cells is carried by the $Ca^{++}$ ions. In contrast, because the concentration of intracellular $Ca^{++}$ is much smaller, only a negligible fraction of the currents that exits the cells is carried by these ions. Thus, $Ca^{++}$ ions accumulate in the cells such that their concentrations in the cells increases, while the concentration in the extracellular compartment may decrease. These effects are observed for both DC and alternating currents (AC). The rate of accumulation of the ions depends on the current intensity ion mobilities, membrane ion conductance, etc. An increase in [$Ca^{++}$] is harmful to most cells and if sufficiently high will lead to the destruction of the cells. Similar considerations apply to other ions. In view of the above observations, long term current application to living organisms or tissues can result in significant damage. Another major problem that is associated with such electric fields, is due to the electrolysis process that takes place at the electrode surfaces. Here charges are transferred between the metal (electrons) and the electrolytic solution (ions) such that charged active radicals are formed. These can cause significant damage to organic molecules, especially macromolecules and thus damage the living cells and tissues.

In contrast, when high frequency electric fields, above 1 MHz and usually in practice in the range of GHz, are induced in tissues by means of insulated electrodes, the situation is quite different. These type of fields generate only capacitive or displacement currents, rather than the conventional charge conducting currents. Under the effect of this type of field, living tissues behave mostly according to their dielectric properties rather than their electric conductive properties. Therefore, the dominant field effect is that due to dielectric losses and heating. Thus, it is widely accepted that in practice, the meaningful effects of such fields on living organisms, are only those due to their heating effects, i.e., due to dielectric losses.

In U.S. Pat. No. 6,043,066 ('066) to Mangano, a method and device are presented which enable discrete objects having a conducting inner core, surrounded by a dielectric membrane to be selectively inactivated by electric fields via irreversible breakdown of their dielectric membrane. One potential application for this is in the selection and purging of certain biological cells in a suspension. According to the '066 patent, an electric field is applied for targeting selected cells to cause breakdown of the dielectric membranes of these tumor cells, while purportedly not adversely affecting other desired subpopulations of cells. The cells are selected on the basis of intrinsic or induced differences in a characteristic electroporation threshold. The differences in this threshold can depend upon a number of parameters, including the difference in cell size.

The method of the '066 patent is therefore based on the assumption that the electroporation threshold of tumor cells is sufficiently distinguishable from that of normal cells because of differences in cell size and differences in the dielectric properties of the cell membranes. Based upon this assumption, the larger size of many types of tumor cells makes these cells more susceptible to electroporation and thus, it may be possible to selectively damage only the larger tumor cell membranes by applying an appropriate electric field. One disadvantage of this method is that the ability to discriminate is highly dependent upon cell type, for example, the size difference between normal cells and tumor cells is significant only in certain types of cells. Another drawback of this method is that the voltages which are applied can damage some of the normal cells and may not damage all of the tumor cells because the differences in size and membrane dielectric properties are largely statistical and the actual cell geometries and dielectric properties can vary significantly.

What is needed in the art and has heretofore not been available is an apparatus for destroying dividing cells, wherein the apparatus better discriminates between dividing cells, including single-celled organisms, and non-dividing cells and is capable of selectively destroying the dividing cells or organisms with substantially no effect on the non-dividing cells or organisms.

SUMMARY

While they are dividing, cells are vulnerable to damage by AC electric fields that have specific frequency and field strength characteristics. The selective destruction of rapidly dividing cells can therefore be accomplished by imposing an AC electric field in a target region for extended periods of time. Some of the cells that divide while the field is applied will be damaged, but the cells that do not divide will not be harmed. This selectively damages rapidly dividing cells like tumor cells, but does not harm normal cells that are not dividing. Since the vulnerability of the dividing cells is strongly related to the alignment between the long axis of the dividing cells and the lines of force of the electric field, improved results are obtained in one preferred embodiment by sequentially imposing the field in different directions.

A major use of the present apparatus is in the treatment of tumors by selective destruction of tumor cells with substantially no effect on normal tissue cells, and thus, the exemplary apparatus is described below in the context of selective destruction of tumor cells. It should be appreciated however, that for purpose of the following description, the term "cell" may also refer to a single-celled organism (eubacteria, bacteria, yeast, protozoa), multi-celled organisms (fungi, algae, mold), and plants as or parts thereof that are not normally classified as "cells". The exemplary apparatus enables selective destruction of cells undergoing division in a way that is more effective and more accurate (e.g., more adaptable to be aimed at specific targets) than existing methods. Further, the present apparatus causes minimal damage, if any, to normal tissue and, thus, reduces or eliminates many side-effects associated with existing selective destruction methods, such as radiation therapy and chemotherapy. The selective destruction of dividing cells using the present apparatus does not depend on the sensitivity of the cells to chemical agents or radiation. Instead, the selective destruction of dividing cells is based on distinguishable geometrical characteristics of cells undergoing division, in comparison to non-dividing cells, regardless of the cell geometry of the type of cells being treated.

According to one exemplary embodiment, cell geometry-dependent selective destruction of living tissue is performed by inducing a non-homogenous electric field in the cells using an electronic apparatus.

It has been observed by the present inventor that, while different cells in their non-dividing state may have different shapes, e.g., spherical, ellipsoidal, cylindrical, "pancake-like", etc., the division process of practically all cells is characterized by development of a "cleavage furrow" in late anaphase and telophase. This cleavage furrow is a slow constriction of the cell membrane (between the two sets of daughter chromosomes) which appears microscopically as a growing cleft (e.g., a groove or notch) that gradually separates the cell into two new cells. During the division process, there is a transient period (telophase) during which the cell structure is basically that of two sub-cells interconnected by a narrow "bridge" formed of the cell material. The division process is completed when the "bridge" between the two sub-cells is broken. The selective destruction of tumor cells using the present electronic apparatus utilizes this unique geometrical feature of dividing cells.

When a cell or a group of cells are under natural conditions or environment, i.e., part of a living tissue, they are disposed surrounded by a conductive environment consisting mostly of an electrolytic inter-cellular fluid and other cells that are composed mostly of an electrolytic intra-cellular liquid. When an electric field is induced in the living tissue, by applying an electric potential across the tissue, an electric field is formed in the tissue and the specific distribution and configuration of the electric field lines defines the direction of charge displacement, or paths of electric currents in the tissue, if currents are in fact induced in the tissue. The distribution and configuration of the electric field is dependent on various parameters of the tissue, including the geometry and the electric properties of the different tissue components, and the relative conductivities, capacities and dielectric constants (that may be frequency dependent) of the tissue components.

The electric current flow pattern for cells undergoing division is very different and unique as compared to non-dividing cells. Such cells including first and second sub-cells, namely an "original" cell and a newly formed cell, that are connected by a cytoplasm "bridge" or "neck". The currents penetrate the first sub-cell through part of the membrane ("the current source pole"); however, they do not exit the first sub-cell through a portion of its membrane closer to the opposite pole ("the current sink pole"). Instead, the lines of current flow converge at the neck or cytoplasm bridge, whereby the density of the current flow lines is greatly increased. A corresponding, "mirror image", process that takes place in the second sub-cell, whereby the current flow lines diverge to a lower density configuration as they depart from the bridge, and finally exit the second sub-cell from a part of its membrane closes to the current sink.

When a polarizable object is placed in a non-uniform converging or diverging field, electric forces act on it and pull it towards the higher density electric field lines. In the case of dividing cell, electric forces are exerted in the direction of the cytoplasm bridge between the two cells. Since all intercellular organelles and macromolecules are polarizable, they are all force towards the bridge between the two cells. The field polarity is irrelevant to the direction of the force and, therefore, an alternating electric having specific properties can be used to produce substantially the same effect. It will also be appreciated that the concentrated and inhomogeneous electric field present in or near the bridge or neck portion in itself exerts strong forces on charges and natural dipoles and can lead to the disruption of structures associated with these members.

The movement of the cellular organelles towards the bridge disrupts the cell structure and results in increased pressure in the vicinity of the connecting bridge membrane. This pressure of the organelles on the bridge membrane is expected to break the bridge membrane and, thus, it is expected that the dividing cell will "explode" in response to this pressure. The ability to break the membrane and disrupt other cell structures can be enhanced by applying a pulsating alternating electric field that has a frequency from about 50 KHz to about 500 KHz. When this type of electric field is applied to the tissue, the forces exerted on the intercellular organelles have a "hammering" effect, whereby force pulses (or beats) are applied to the organelles numerous times per second, enhancing the movement of organelles of different sizes and masses towards the bridge (or neck) portion from both of the sub-cells, thereby increasing the probability of breaking the cell membrane at the bridge portion. The forces exerted on the intracellular organelles also affect the organelles themselves and may collapse or break the organelles.

According to one exemplary embodiment, the apparatus for applying the electric field is an electronic apparatus that generates the desired electric signals in the shape of waveforms or trains of pulses. The electronic apparatus includes a generator that generates an alternating voltage waveform at frequencies in the range from about 50 KHz to about 500 KHz. The generator is operatively connected to conductive leads which are connected at their other ends to insulated conductors/electrodes (also referred to as isolects) that are activated by the generated waveforms. The insulated electrodes consist of a conductor in contact with a dielectric (insulating layer) that is in contact with the conductive tissue, thus forming a capacitor. The electric fields that are generated by the present apparatus can be applied in several different modes depending upon the precise treatment application.

In one exemplary embodiment, the electric fields are applied by external insulated electrodes which are incorporated into an article of clothing and which are constructed so that the applied electric fields are of a local type that target a specific, localized area of tissue (e.g., a tumor). This embodiment is designed to treat tumors and lesions that are at or below the skin surface by wearing the article of clothing over the target tissue so that the electric fields generated by the insulated electrodes are directed at the tumors (lesions, etc.).

According to another embodiment, the apparatus is used in an internal type application in that the insulated electrodes are in the form of a probe or catheter etc., that enter the body through natural pathways, such as the urethra or vagina, or are configured to penetrate living tissue, until the insulated electrodes are positioned near the internal target area (e.g., an internal tumor).

Thus, the present apparatus utilizes electric fields that fall into a special intermediate category relative to previous high and low frequency applications in that the present electric fields are bio-effective fields that have no meaningful stimulatory effects and no thermal effects. Advantageously, when non-dividing cells are subjected to these electric fields, there is no effect on the cells; however, the situation is much different when dividing cells are subjected to the present electric fields. Thus, the present electronic apparatus and the generated electric fields target dividing cells, such as tumors or the like, and do not target non-dividing cells that is found around in healthy tissue surrounding the target area. Furthermore, since the present apparatus utilizes insulated electrodes, the above mentioned negative effects, obtained when conductive electrodes are used, i.e., ion concentration changes in the cells and the formation of harmful agents by electrolysis, do not occur with the present apparatus. This is because, in general, no actual transfer of charges takes place between the electrodes and the medium, and there is no charge flow in the medium where the currents are capacitive.

It should be appreciated that the present electronic apparatus can also be used in applications other than treatment of tumors in the living body. In fact, the selective destruction utilizing the present apparatus can be used in conjunction with any organism that proliferates by division, for example, tissue cultures, microorganisms, such as bacteria, mycoplasma, protozoa, fungi, algae, plant cells, etc. Such organisms divide by the formation of a groove or cleft as described above. As the groove or cleft deepens, a narrow bridge is formed between the two parts of the organism, similar to the bridge formed between the sub-cells of dividing animal cells. Since such organisms are covered by a membrane having a relatively low electric conductivity, similar to an animal cell membrane described above, the electric field lines in a dividing organism converge at the bridge connecting the two parts of the dividing organism. The converging field lines result in electric forces that displace polarizable elements and charges within the dividing organism.

The above, and other objects, features and advantages of the present apparatus will become apparent from the following description read in conjunction with the accompanying drawings, in which like reference numerals designate the same elements.

BRIEF DESCRIPTION OF THE DRAWINGS

FIG. 7 is a cross-sectional illustration of a skin patch incorporating the apparatus of FIG. 5 and for placement on a skin surface for treating a tumor or the like;

FIG. 8 is a cross-sectional illustration of the insulated electrodes implanted within the body for treating a tumor or the like;

FIG. 9 is a cross-sectional illustration of the insulated electrodes implanted within the body for treating a tumor or the like;

FIG. 14 is a cross-sectional view of insulated electrodes incorporated into a hat according to a first embodiment for placement on a head for treating an intra-cranial tumor or the like;

FIG. 17 is a cross-sectional top view of an article of clothing having the insulated electrodes incorporated therein for treating a tumor or the like;

FIG. 19 is a cross-sectional view of a probe according to one embodiment for being disposed internally within the body for treating a tumor or the like;

DETAILED DESCRIPTION OF PREFERRED EMBODIMENTS

Figure 1A:
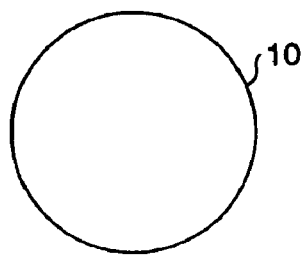
FIGS. 1A-1E are simplified, schematic, cross-sectional, illustrations of various stages of a cell division process.
Figure 1B:
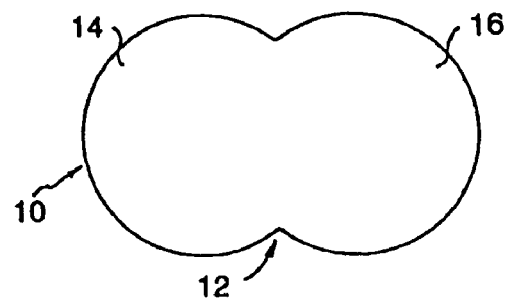
Figure 1C:
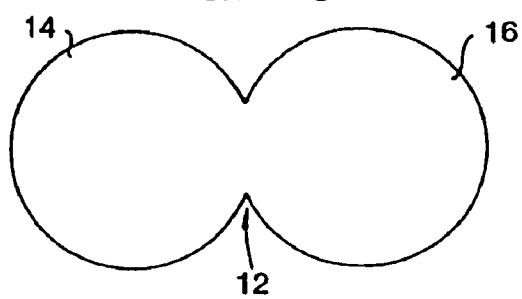
Figure 1D:
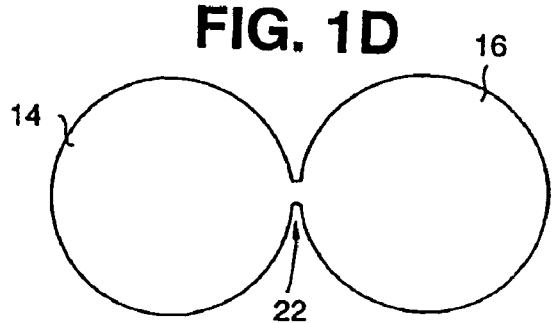

Reference is made to FIGS. 1A-1E which schematically illustrate various stages of a cell division process. FIG. 1A illustrates a cell 10 at its normal geometry, which can be generally spherical (as illustrated in the drawings), ellipsoidal, cylindrical, "pancake-like" or any other cell geometry, as is known in the art. FIGS. 1B-1D illustrate cell 10 during different stages of its division process, which results in the formation of two new cells 18 and 20, shown in FIG. 1E.

Figure 1E:
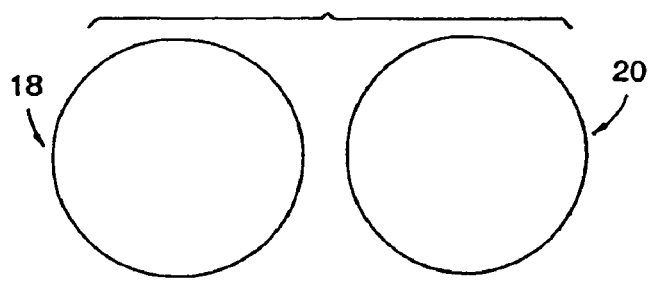

As shown in FIGS. 1B-1D, the division process of cell 10 is characterized by a slowly growing cleft 12 which gradually separates cell 10 into two units, namely sub-cells 14 and 16, which eventually evolve into new cells 18 and 20 (FIG. 1E). A shown specifically in FIG. 1D, the division process is characterized by a transient period during which the structure of cell 10 is basically that of the two sub-cells 14 and 16 interconnected by a narrow "bridge" 22 containing cell material (cytoplasm surrounded by cell membrane).

Figure 2A:
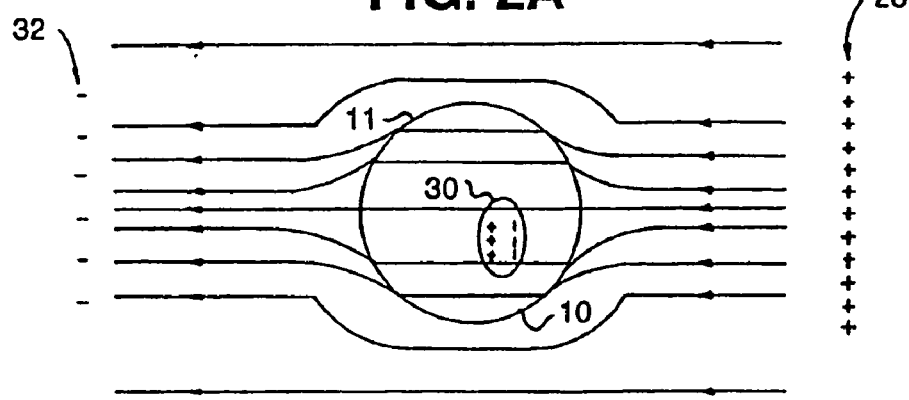
FIGS. 2A and 2B are schematic illustrations of a non-dividing cell being subjected to an electric field.
Figure 2B:
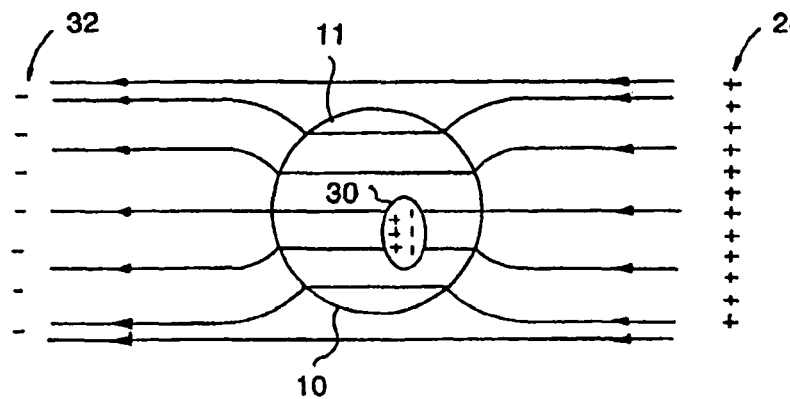

Reference is now made to FIGS. 2A and 2B, which schematically illustrate non-dividing cell 10 being subjected to an electric field produced by applying an alternating electric potential, at a relatively low frequency and at a relatively high frequency, respectively. Cell 10 includes intracellular organelles, e.g., a nucleus 30. Alternating electric potential is applied across electrodes 28 and 32 that can be attached externally to a patient at a predetermined region, e.g., in the vicinity of the tumor being treated. When cell 10 is under natural conditions, i.e., part of a living tissue, it is disposed in a conductive environment (hereinafter referred to as a "volume conductor") consisting mostly of electrolytic inter-cellular liquid. When an electric potential is applied across electrodes 28 and 32, some of the field lines of the resultant electric field (or the current induced in the tissue in response to the electric field) penetrate the cell 10, while the rest of the field lines (or induced current) flow in the surrounding medium. The specific distribution of the electric field lines, which is substantially consistent with the direction of current flow in this instance, depends on the geometry and the electric properties of the system components, e.g., the relative conductivities and dielectric constants of the system components, that can be frequency dependent. For low frequencies, e.g., frequencies lower than 10 KHz, the conductance properties of the components completely dominate the current flow and the field distribution, and the field distribution is generally as depicted in FIG. 2A. At higher frequencies, e.g., at frequencies of between 10 KHz and 1 MHz, the dielectric properties of the components becomes more significant and eventually dominate the field distribution, resulting in field distribution lines as depicted generally in FIG. 2B.

For constant (i.e., DC) electric fields or relatively low frequency alternating electric fields, for example, frequencies under 10 KHz, the dielectric properties of the various components are not significant in determining and computing the field distribution. Therefore, as a first approximation, with regard to the electric field distribution, the system can be reasonably represented by the relative impedances of its various components. Using this approximation, the intercellular (i.e., extracellular) fluid and the intracellular fluid each has a relatively low impedance, while the cell membrane 11 has a relatively high impedance. Thus, under low frequency conditions, only a fraction of the electric field lines (or currents induced by the electric field) penetrate membrane 11 of the cell 10. At relatively high frequencies (e.g., 10 KHz-1 MHz), in contrast, the impedance of membrane 11 relative to the intercellular and intracellular fluids decreases, and thus, the fraction of currents penetrating the cells increases significantly. It should be noted that at very high frequencies, i.e., above 1 MHz, the membrane capacitance can short the membrane resistance and, therefore, the total membrane resistance can become negligible.

In any of the embodiments described above, the electric field lines (or induced currents) penetrate cell 10 from a portion of the membrane 11 closest to one of the electrodes generating the current, e.g., closest to positive electrode 28 (also referred to herein as "source"). The current flow pattern across cell 10 is generally uniform because, under the above approximation, the field induced inside the cell is substantially homogeneous. The currents exit cell 10 through a portion of membrane 11 closest to the opposite electrode, e.g., negative electrode 32 (also referred to herein as "sink").

The distinction between field lines and current flow can depend on a number of factors, for example, on the frequency of the applied electric potential and on whether electrodes 28 and 32 are electrically insulated. For insulated electrodes applying a DC or low frequency alternating voltage, there is practically no current flow along the lines of the electric field. At higher frequencies, the displacement currents are induced in the tissue due to charging and discharging of the electrode insulation and the cell membranes (which act as capacitors to a certain extent), and such currents follow the lines of the electric field. Fields generated by non-insulated electrodes, in contrast, always generate some form of current flow, specifically, DC or low frequency alternating fields generate conductive current flow along the field lines, and high frequency alternating fields generate both conduction and displacement currents along the field lines. It should be appreciated, however, that movement of polarizable intracellular organelles according to the present invention (as described below) is not dependent on actual flow of current and, therefore, both insulated and non-insulated electrodes can be used efficiently. Advantages of insulated electrodes include lower power consumption, less heating of the treated regions, and improved patient safety.

According to one exemplary embodiment of the present invention, the electric fields that are used are alternating fields having frequencies that are in the range from about 50 KHz to about 500 KHz, and preferably from about 100 KHz to about 300 KHz. For ease of discussion, these type of electric fields are also referred to below as "TC fields", which is an abbreviation of "Tumor Curing electric fields", since these electric fields fall into an intermediate category (between high and low frequency ranges) that have bio-effective field properties while having no meaningful stimulatory and thermal effects. These frequencies are sufficiently low so that the system behavior is determined by the system's Ohmic (conductive) properties but sufficiently high enough not to have any stimulation effect on excitable tissues. Such a system consists of two types of elements, namely, the intercellular, or extracellular fluid, or medium and the individual cells. The intercellular fluid is mostly an electrolyte with a specific resistance of about 40-100 Ohm*cm. As mentioned above, the cells are characterized by three elements, namely (1) a thin, highly electric resistive membrane that coats the cell; (2) internal cytoplasm that is mostly an electrolyte that contains numerous macromolecules and micro-organelles, including the nucleus; and (3) membranes, similar in their electric properties to the cell membrane, cover the micro-organelles.

When this type of system is subjected to the present TC fields (e.g., alternating electric fields in the frequency range of 100 KHz-300 KHz) most of the lines of the electric field and currents tend away from the cells because of the high resistive cell membrane and therefore the lines remain in the extracellular conductive medium. In the above recited frequency range, the actual fraction of electric field or currents that penetrates the cells is a strong function of the frequency.

FIG. 2 schematically depicts the resulting field distribution in the system. As illustrated, the lines of force, which also depict the lines of potential current flow across the cell volume mostly in parallel with the undistorted lines of force (the main direction of the electric field). In other words, the field inside the cells is mostly homogeneous. In practice, the fraction of the field or current that penetrates the cells is determined by the cell membrane impedance value relative to that of the extracellular fluid. Since the equivalent electric circuit of the cell membrane is that of a resistor and capacitor in parallel, the impedance is a function of the frequency. The higher the frequency, the lower the impedance, the larger the fraction of penetrating current and the smaller the field distortion (Rotshenker S. & Y. Palti, *Changes in fraction of current penetrating an axon as a function of duration of stimulating pulse*, J. Theor. Biol. 41; 401-407 (1973).

As previously mentioned, when cells are subjected to relatively weak electric fields and currents that alternate at high frequencies, such as the present TC fields having a frequency in the range of 50 KHz-500 KHz, they have no effect on the non-dividing cells. While the present TC fields have no detectable effect on such systems, the situation becomes different in the presence of dividing cells.

Figure 3A:
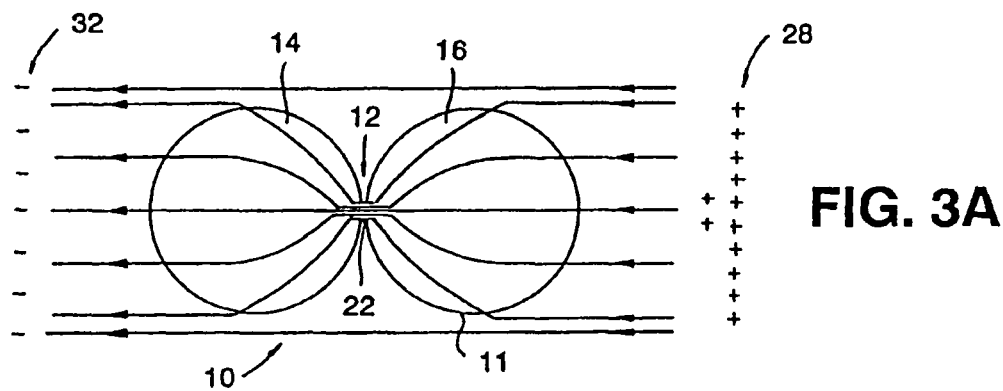
FIGS. 3A, 3B and 3C are schematic illustrations of a dividing cell being subjected to an electric field according to one exemplary embodiment, resulting in destruction of the cell (FIG. 3C) in accordance with one exemplary embodiment.
Figure 3B:
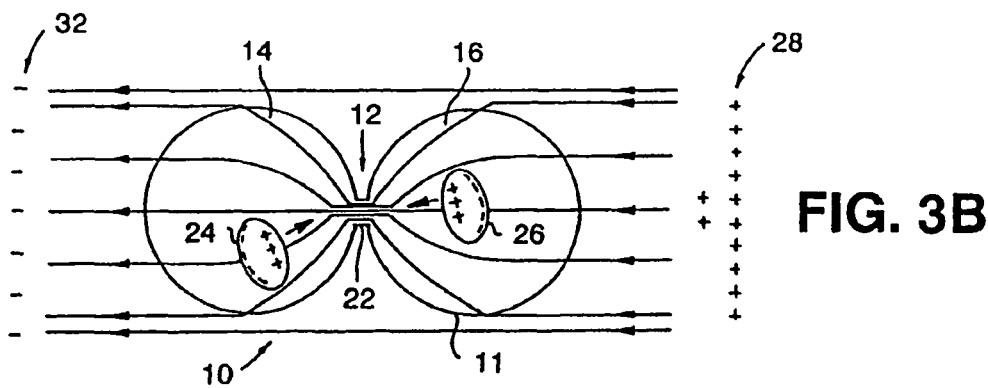
Figure 3C:
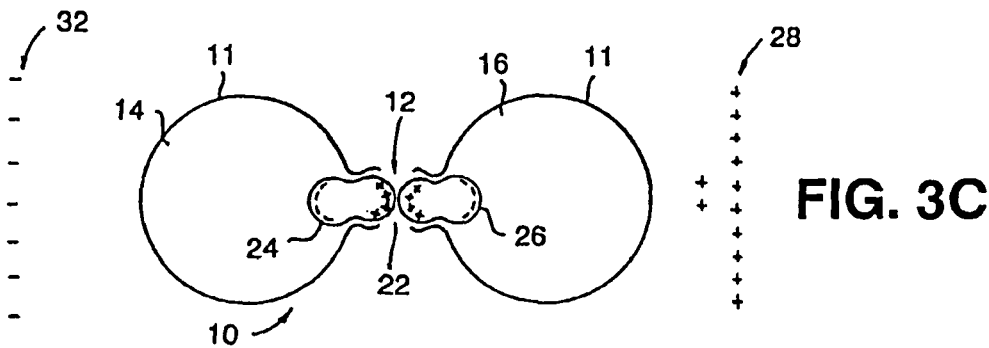

Reference is now made to FIGS. 3A-3C which schematically illustrate the electric current flow pattern in cell 10 during its division process, under the influence of alternating fields (TC fields) in the frequency range from about 100 KHz to about 300 KHz in accordance with one exemplary embodiment. The field lines or induced currents penetrate cell 10 through a part of the membrane of sub-cell 16 closer to electrode 28. However, they do not exit through the cytoplasm bridge 22 that connects sub-cell 16 with the newly formed yet still attached sub-cell 14, or through a part of the membrane in the vicinity of the bridge 22. Instead, the electric field or current flow lines—that are relatively widely separated in sub-cell 16—converge as they approach bridge 22 (also referred to as "neck" 22) and, thus, the current/field line density within neck 22 is increased dramatically. A "mirror image" process takes place in sub-cell 14, whereby the converging field lines in bridge 22 diverge as they approach the exit region of sub-cell 14.

It should be appreciated by persons skilled in the art that homogeneous electric fields do not exert a force on electrically neutral objects, i.e., objects having substantially zero net charge, although such objects can become polarized. However, under a non-uniform, converging electric field, as shown in FIGS. 3A-3C, electric forces are exerted on polarized objects, moving them in the direction of the higher density electric field lines. It will be appreciated that the concentrated electric field that is present in the neck or bridge area in itself exerts strong forces on charges and natural dipoles and can disrupt structures that are associated therewith. One will understand that similar net forces act on charges in an alternating field, again in the direction of the field of higher intensity.

In the configuration of FIGS. 3A and 3B, the direction of movement of polarized and charged objects is towards the higher density electric field lines, i.e., towards the cytoplasm bridge 22 between sub-cells 14 and 16. It is known in the art that all intracellular organelles, for example, nuclei 24 and 26 of sub-cells 14 and 16, respectively, are polarizable and, thus, such intracellular organelles are electrically forced in the direction of the bridge 22. Since the movement is always from lower density currents to the higher density currents, regardless of the field polarity, the forces applied by the alternating electric field to organelles, such as nuclei 24 and 26, are always in the direction of bridge 22. A comprehensive description of such forces and the resulting movement of macromolecules of intracellular organelles, a phenomenon referred to as "dielectrophoresis" is described extensively in literature, e.g., in C. L. Asbury & G. van den Engh, Biophys. J. 74, 1024-1030, 1998, the disclosure of which is hereby incorporated by reference in its entirety.

The movement of the organelles 24 and 26 towards the bridge 22 disrupts the structure of the dividing cell, change the concentration of the various cell constituents and, eventually, the pressure of the converging organelles on bridge membrane 22 results in the breakage of cell membrane 11 at the vicinity of the bridge 22, as shown schematically in FIG. 3C. The ability to break membrane 11 at bridge 22 and to otherwise disrupt the cell structure and organization can be enhanced by applying a pulsating AC electric field, rather than a steady AC field. When a pulsating field is applied, the forces acting on organelles 24 and 26 have a "hammering" effect, whereby pulsed forces beat on the intracellular organelles towards the neck 22 from both sub-cells 14 and 16, thereby increasing the probability of breaking cell membrane 11 in the vicinity of neck 22.

Figure 4:
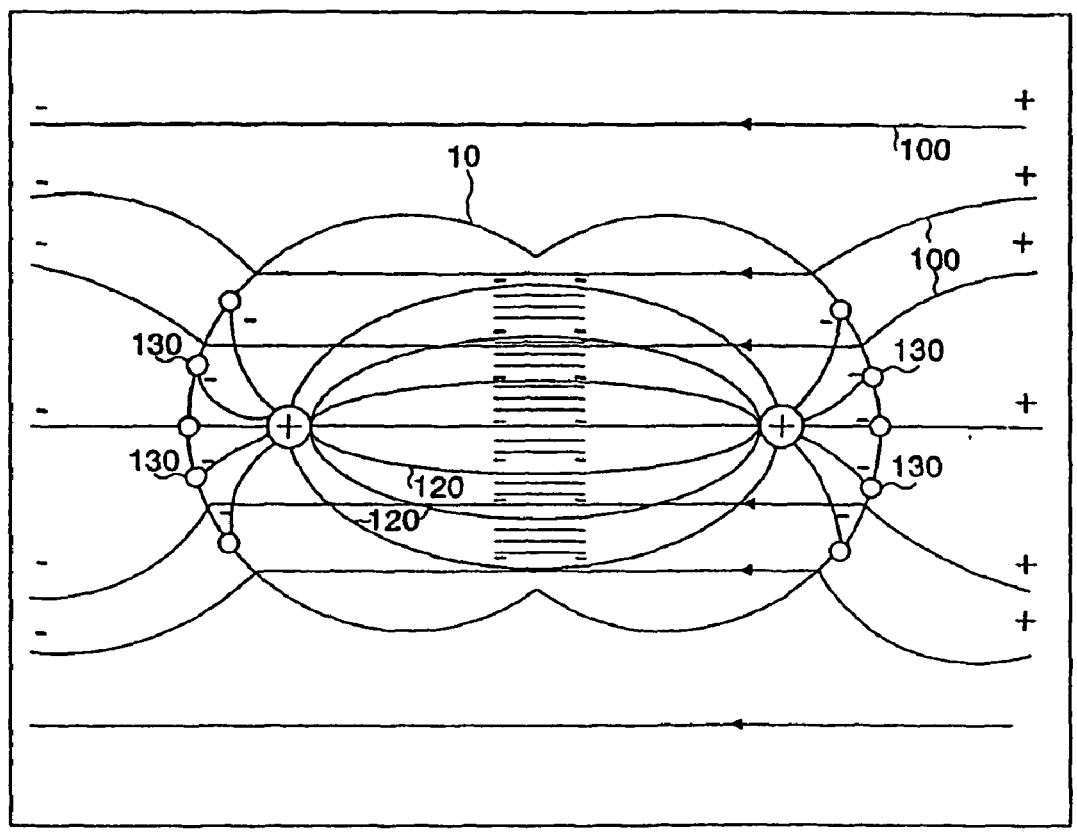
FIG. 4 is a schematic illustration of a dividing cell at one stage being subject to an electric field.

A very important element, which is very susceptible to the special fields that develop within the dividing cells is the microtubule spindle that plays a major role in the division process. In FIG. 4, a dividing cell 10 is illustrated, at an earlier stage as compared to FIGS. 3A and 3B, under the influence of external TC fields (e.g., alternating fields in the frequency range of about 100 KHz to about 300 KHz), generally indicated as lines 100, with a corresponding spindle mechanism generally indicated at 120. The lines 120 are microtubules that are known to have a very strong dipole moment. This strong polarization makes the tubules, as well as other polar macromolecules and especially those that have a specific orientation within the cells or its surrounding, susceptible to electric fields. Their positive charges are located at the two centrioles while two sets of negative poles are at the center of the dividing cell and the other pair is at the points of attachment of the microtubules to the cell membrane, generally indicated at 130. This structure forms sets of double dipoles and therefore they are susceptible to fields of different directions. It will be understood that the effect of the TC fields on the dipoles does not depend on the formation of the bridge (neck) and thus, the dipoles are influenced by the TC fields prior to the formation of the bridge (neck).

Since the present apparatus (as will be described in greater detail below) utilizes insulated electrodes, the above-mentioned negative effects obtained when conductive electrodes are used, i.e., ion concentration changes in the cells and the formation of harmful agents by electrolysis, do not occur when the present apparatus is used. This is because, in general, no actual transfer of charges takes place between the electrodes and the medium and there is no charge flow in the medium where the currents are capacitive, i.e., are expressed only as rotation of charges, etc.

Figure 5:
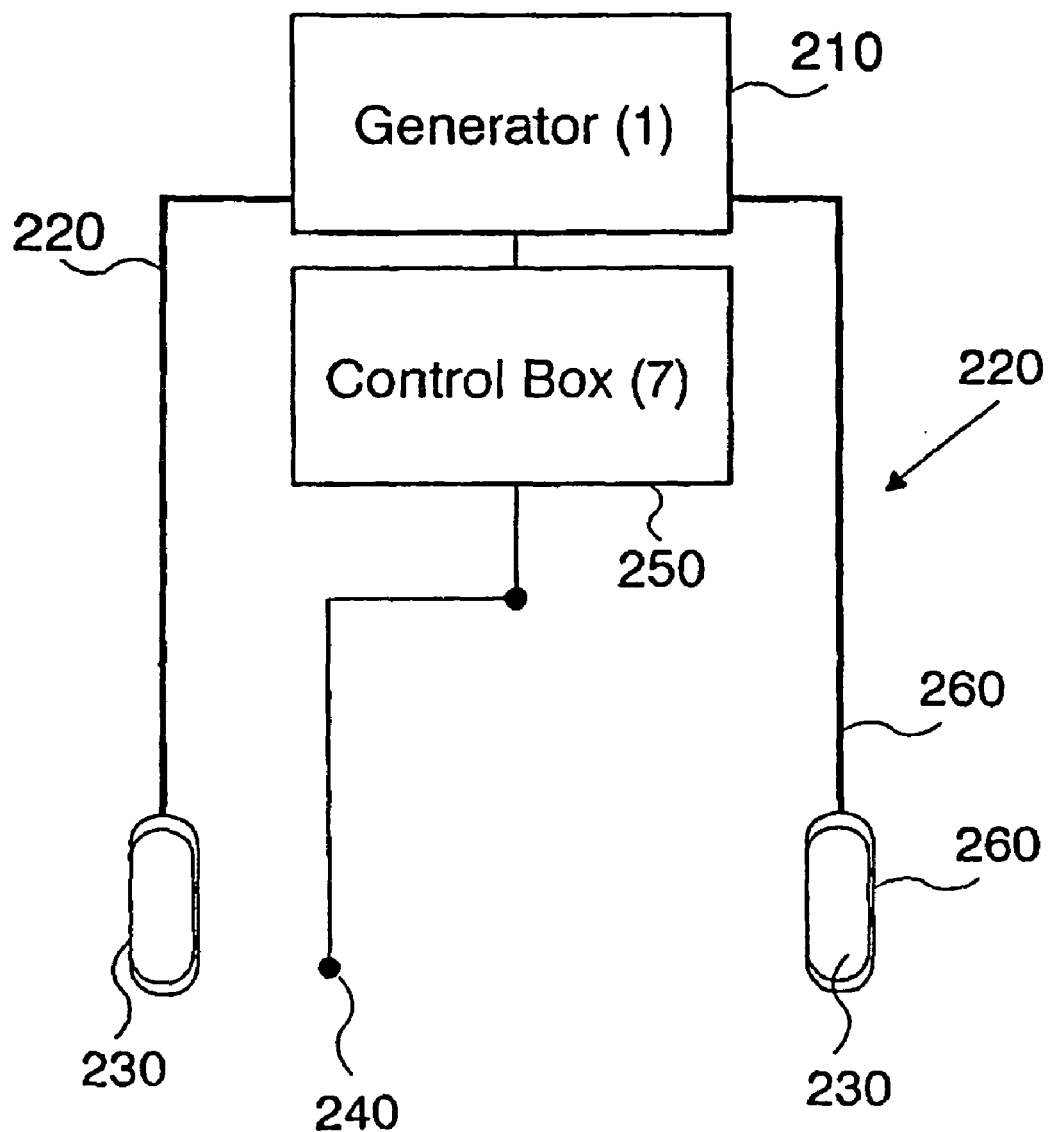
FIG. 5 is a schematic block diagram of an apparatus for applying an electric according to one exemplary embodiment for selectively destroying cells.

Turning now to FIG. 5, the TC fields described above that have been found to advantageously destroy tumor cells are generated by an electronic apparatus 200. FIG. 5 is a simple schematic diagram of the electronic apparatus 200 illustrating the major components thereof. The electronic apparatus 200 generates the desired electric signals (TC signals) in the shape of waveforms or trains of pulses. The apparatus 200 includes a generator 210 and a pair of conductive leads 220 that are attached at one end thereof to the generator 210. The opposite ends of the leads 220 are connected to insulated conductors 230 that are activated by the electric signals (e.g., waveforms). The insulated conductors 230 are also referred to hereinafter as isolects 230. Optionally and according to another exemplary embodiment, the apparatus 200 includes a temperature sensor 240 and a control box 250 which are both added to control the amplitude of the electric field generated so as not to generate excessive heating in the area that is treated.

The generator 210 generates an alternating voltage waveform at frequencies in the range from about 50 KHz to about 500 KHz (preferably from about 100 KHz to about 300 KHz) (i.e., the TC fields). The required voltages are such that the electric field intensity in the tissue to be treated is in the range of about 0.1 V/cm to about 10 V/cm. To achieve this field, the actual potential difference between the two conductors in the isolects 230 is determined by the relative impedances of the system components, as described below.

When the control box 250 is included, it controls the output of the generator 210 so that it will remain constant at the value preset by the user or the control box 250 sets the output at the maximal value that does not cause excessive heating, or the control box 250 issues a warning or the like when the temperature (sensed by temperature sensor 240) exceeds a preset limit.

The leads 220 are standard isolated conductors with a flexible metal shield, preferably grounded so that it prevents the spread of the electric field generated by the leads 220. The isolects 230 have specific shapes and positioning so as to generate an electric field of the desired configuration, direction and intensity at the target volume and only there so as to focus the treatment.

The specifications of the apparatus 200 as a whole and its individual components are largely influenced by the fact that at the frequency of the present TC fields (50 KHz-500 KHz), living systems behave according to their "Ohmic", rather than their dielectric properties. The only elements in the apparatus 200 that behave differently are the insulators of the isolects 230 (see FIGS. 7-9). The isolects 200 consist of a conductor in contact with a dielectric that is in contact with the conductive tissue thus forming a capacitor.

Figure 6:
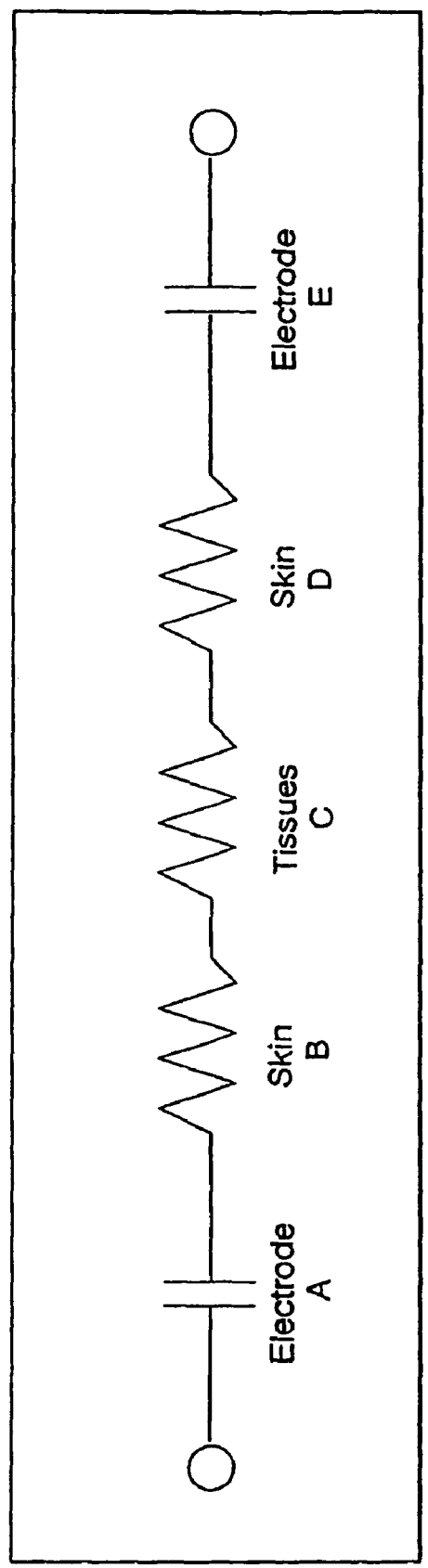
FIG. 6 is a simplified schematic diagram of an equivalent electric circuit of insulated electrodes of the apparatus of FIG. 5.

The details of the construction of the isolects 230 is based on their electric behavior that can be understood from their simplified electric circuit when in contact with tissue as generally illustrated in FIG. 6. In the illustrated arrangement, the potential drop or the electric field distribution between the different components is determined by their relative electric impedance, i.e., the fraction of the field on each component is given by the value of its impedance divided by the total circuit impedance. For example, the potential drop on element Δ $V_A=A/(A+B+C+D+E)$. Thus, for DC or low frequency AC, practically all the potential drop is on the capacitor (that acts as an insulator). For relatively very high frequencies, the capacitor practically is a short and therefore, practically all the field is distributed in the tissues. At the frequencies of the present TC fields (e.g., 50 KHz to 500 KHz), which are intermediate frequencies, the impedance of the capacitance of the capacitors is dominant and determines the field distribution. Therefore, in order to increase the effective voltage drop across the tissues (field intensity), the impedance of the capacitors is to be decreased (i.e., increase their capacitance). This can be achieved by increasing the effective area of the "plates" of the capacitor, decrease the thickness of the dielectric or use a dielectric with high dielectric constant.

In order to optimize the field distribution, the isolects 230 are configured differently depending upon the application in which the isolects 230 are to be used. There are two principle modes for applying the present electric fields (TC fields). First, the TC fields can be applied by external isolects and second, the TC fields can be applied by internal isolects.

Figure 7:
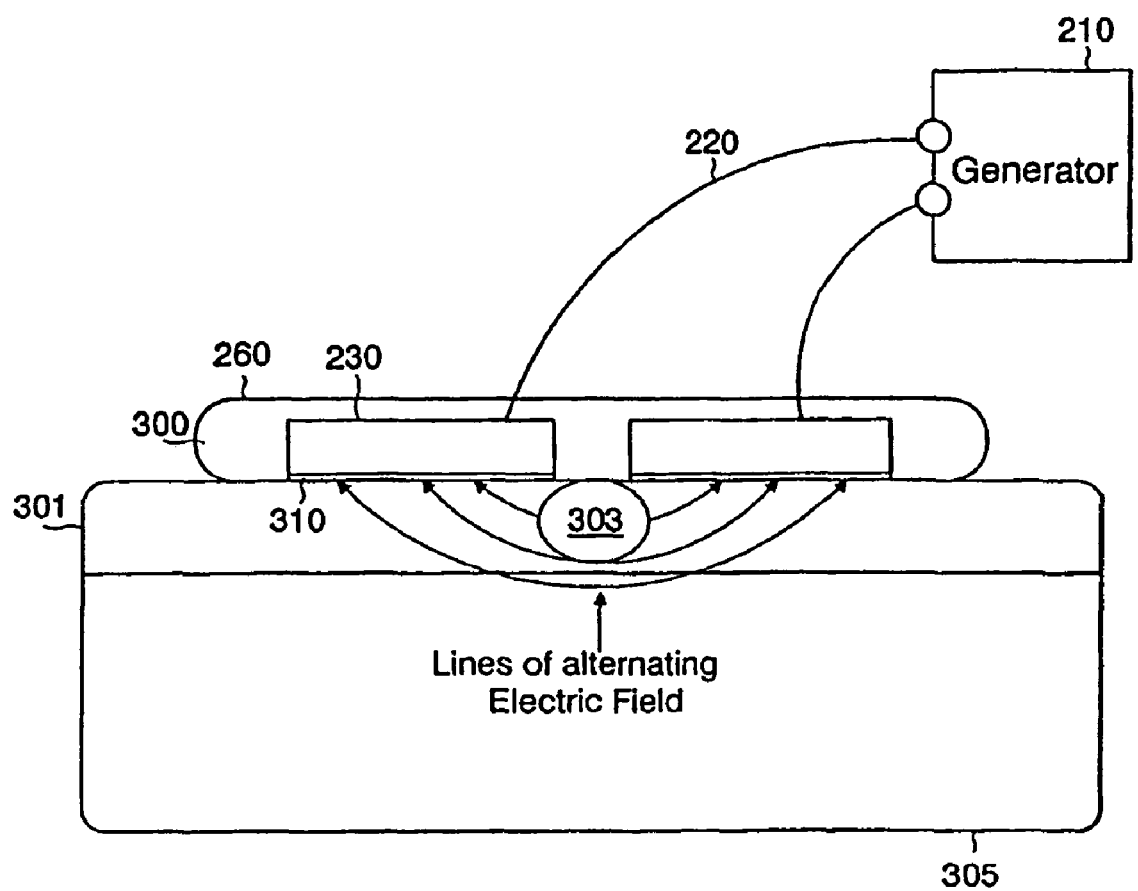

Electric fields (TC fields) that are applied by external isolects can be of a local type or widely distributed type. The first type includes, for example, the treatment of skin tumors and treatment of lesions close to the skin surface. FIG. 7 illustrates an exemplary embodiment where the isolects 230 are incorporated in a skin patch 300. The skin patch 300 can be a self-adhesive flexible patch with one or more pairs of isolects 230. The patch 300 includes internal insulation 310 (formed of a dielectric material) and the external insulation 260 and is applied to skin surface 301 that contains a tumor 303 either on the skin surface 301 or slightly below the skin surface 301. Tissue is generally indicated at 305. To prevent the potential drop across the internal insulation 310 to dominate the system, the internal insulation 310 must have a relatively high capacity. This can be achieved by a large surface area; however, this may not be desired as it will result in the spread of the field over a large area (e.g., an area larger than required to treat the tumor). Alternatively, the internal insulation 310 can be made very thin and/or the internal insulation 310 can be of a high dielectric constant. As the skin resistance between the electrodes (labeled as A and E in FIG. 6) is normally significantly higher than that of the tissue (labeled as C in FIG. 6) underneath it (1-10 K$\Omega$ vs. 0.1-1 K$\Omega$), most of the potential drop beyond the isolects occurs there. To accommodate for these impedances (Z), the characteristics of the internal insulation 310 (labeled as B and D in FIG. 6) should be such that they have impedance preferably under 100 K$\Omega$ at the frequencies of the present TC fields (e.g., 50 KHz to 500 KHz). For example, if it is desired for the impedance to be about 10 K Ohms or less, such that over 1% of the applied voltage falls on the tissues, for isolects with a surface area of 10 mm$^2$, at frequencies of 200 KHz, the capacity should be on the order of $10^{-10}$ F., which means that using standard insulations with a dielectric constant of 2-3, the thickness of the insulating layer 310 should be about 50-100 microns. An internal field 10 times stronger would be obtained with insulators with a dielectric constant of about 20-50.

Using an insulating material with a high dielectric constant increases the capacitance of the electrodes, which results in a reduction of the electrodes' impedance to the AC signal that is applied by the generator 1 (shown in FIG. 5). Because the electrodes A, E are wired in series with the target tissue C, as shown in FIG. 6, this reduction in impedance reduces the voltage drop in the electrodes, so that a larger portion of the applied AC voltage appears across the tissue C. Since a larger portion of the voltage appears across the tissue, the voltage that is being applied by the generator 1 can be advantageously lowered for a given field strength in the tissue.

The desired field strength in the tissue being treated is preferably between about 0.1 V/cm and about 10 V/cm, and more preferably between about 2 V/cm and 3 V/cm or between about 1 V/cm and about 5 V/cm. If the dielectric constant used in the electrode is sufficiently high, the impedance of the electrodes A, E drops down to the same order of magnitude as the series combination of the skin and tissue B, C, D. One example of a suitable material with an extremely high dielectric constant is $CaCu_3Ti_4O_{12}$, which has a dielectric constant of about 11,000 (measured at 100 kHz). When the dielectric constant is this high, useful fields can be obtained using a generator voltage that is on the order of a few tens of Volts.

Since the thin insulating layer can be very vulnerable, etc., the insulation can be replaced by very high dielectric constant insulating materials, such as titanium dioxide (e.g., rutile), the dielectric constant can reach values of about 200. There a number of different materials that are suitable for use in the intended application and have high dielectric constants. For example, some materials include: lithium niobate ($LiNbO_3$), which is a ferroelectric crystal and has a number of applications in optical, pyroelectric and piezoelectric devices; yttrium iron garnet (YIG) is a ferromagnetic crystal and magneto-optical devices, e.g., optical isolator can be realized from this material; barium titanate ($BaTiO_3$) is a ferromagnetic crystal with a large electro-optic effect; potassium tantalate ($KTaO_3$) which is a dielectric crystal (ferroelectric at low temperature) and has very low microwave loss and tunability of dielectric constant at low temperature; and lithium tantalate ($LiTaO_3$) which is a ferroelectric crystal with similar properties as lithium niobate and has utility in electro-optical, pyroelectric and piezoelectric devices. Insulator ceramics with high dielectric constants may also be used, such as a ceramic made of a combination of Lead Magnesium Niobate and Lead Titanate. It will be understood that the aforementioned exemplary materials can be used in combination with the present device where it is desired to use a material having a high dielectric constant.

Figure 10:
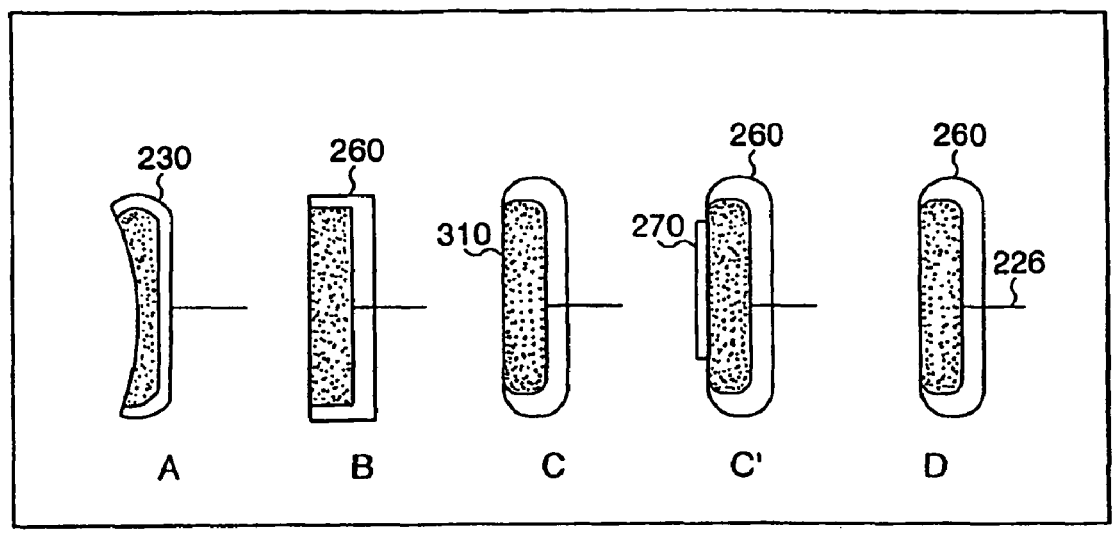
FIGS. 10A-10D are cross-sectional illustrations of various constructions of the insulated electrodes of the apparatus of FIG. 5.

One must also consider another factor that affects the effective capacity of the isolects 230, namely the presence of air between the isolects 230 and the skin. Such presence, which is not easy to prevent, introduces a layer of an insulator with a dielectric constant of 1.0, a factor that significantly lowers the effective capacity of the isolects 230 and neutralizes the advantages of the titanium dioxide (rutile), etc. To overcome this problem, the isolects 230 can be shaped so as to conform with the body structure and/or (2) an intervening filler 270 (as illustrated in FIG. 10C), such as a gel, that has high conductance and a high effective dielectric constant, can be added to the structure. The shaping can be pre-structured (see FIG. 10A) or the system can be made sufficiently flexible so that shaping of the isolects 230 is readily achievable. The gel can be contained in place by having an elevated rim as depicted in FIGS. 10C and 10C'. The gel can be made of hydrogels, gelatins, agar, etc., and can have salts dissolved in it to increase its conductivity. FIGS. 10A-10C' illustrate various exemplary configurations for the isolects 230. The exact thickness of the gel is not important so long as it is of sufficient thickness that the gel layer does not dry out during the treatment. In one exemplary embodiment, the thickness of the gel is about 0.5 mm to about 2 mm. Preferably, the gel has high conductivity, is tacky, and is biocompatible for extended periods of time. One suitable gel is AG603 Hydrogel, which is available from AmGel Technologies, 1667 S. Mission Road, Fallbrook, Calif. 92028-4115, USA.

Figure 12:
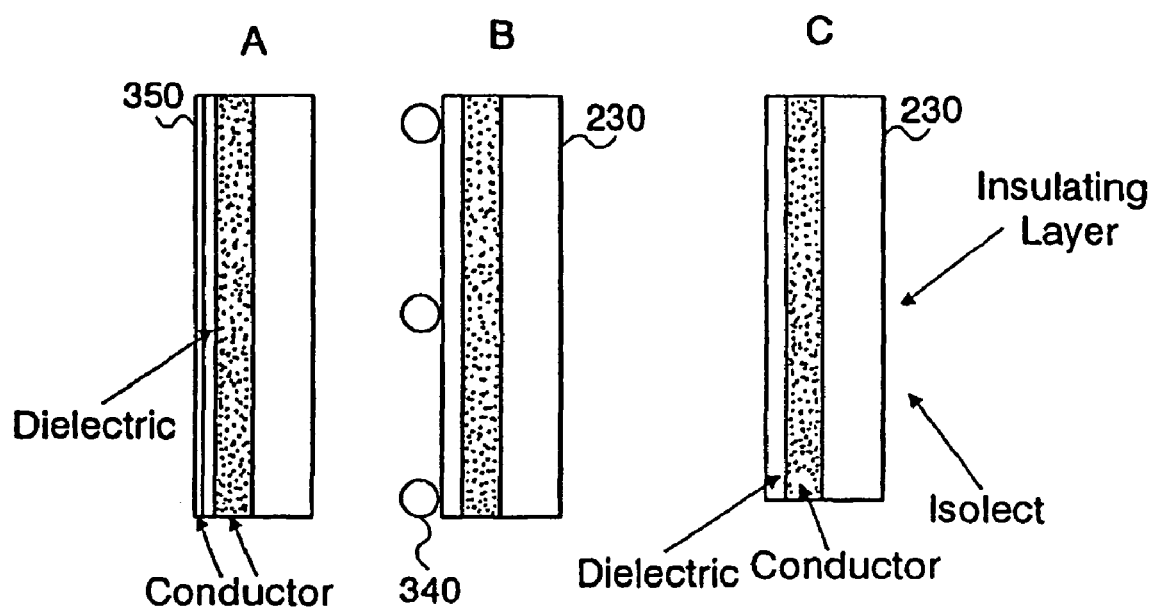
FIGS. 12A-12C are cross-sectional illustrations of various insulated electrodes with and without protective members formed as a part of the construction thereof.

In order to achieve the desirable features of the isolects 230, the dielectric coating of each should be very thin, for example from between 1-50 microns. Since the coating is so thin, the isolects 230 can easily be damaged mechanically or undergo dielectric breakdown. This problem can be overcome by adding a protective feature to the isolect's structure so as to provide desired protection from such damage. For example, the isolect 230 can be coated, for example, with a relatively loose net 340 that prevents access to the surface but has only a minor effect on the effective surface area of the isolect 230 (i.e., the capacity of the isolects 230 (cross section presented in FIG. 12B). The loose net 340 does not effect the capacity and ensures good contact with the skin, etc. The loose net 340 can be formed of a number of different materials; however, in one exemplary embodiment, the net 340 is formed of nylon, polyester, cotton, etc. Alternatively, a very thin conductive coating 350 can be applied to the dielectric portion (insulating layer) of the isolect 230. One exemplary conductive coating is formed of a metal and more particularly of gold. The thickness of the coating 350 depends upon the particular application and also on the type of material used to form the coating 350; however, when gold is used, the coating has a thickness from about 0.1 micron to about 0.1 mm. Furthermore, the rim illustrated in FIG. 10 can also provide some mechanical protection.

However, the capacity is not the only factor to be considered. The following two factors also influence how the isolects 230 are constructed. The dielectric strength of the internal insulating layer 310 and the dielectric losses that occur when it is subjected to the TC field, i.e., the amount of heat generated. The dielectric strength of the internal insulation 310 determines at what field intensity the insulation will be "shorted" and cease to act as an intact insulation. Typically, insulators, such as plastics, have dielectric strength values of about 100V per micron or more. As a high dielectric constant reduces the field within the internal insulator 310, a combination of a high dielectric constant and a high dielectric strength gives a significant advantage. This can be achieved by using a single material that has the desired properties or it can be achieved by a double layer with the correct parameters and thickness. In addition, to further decreasing the possibility that the insulating layer 310 will fail, all sharp edges of the insulating layer 310 should be eliminated as by rounding the corners, etc., as illustrated in FIG. 10D using conventional techniques.

Figure 8:
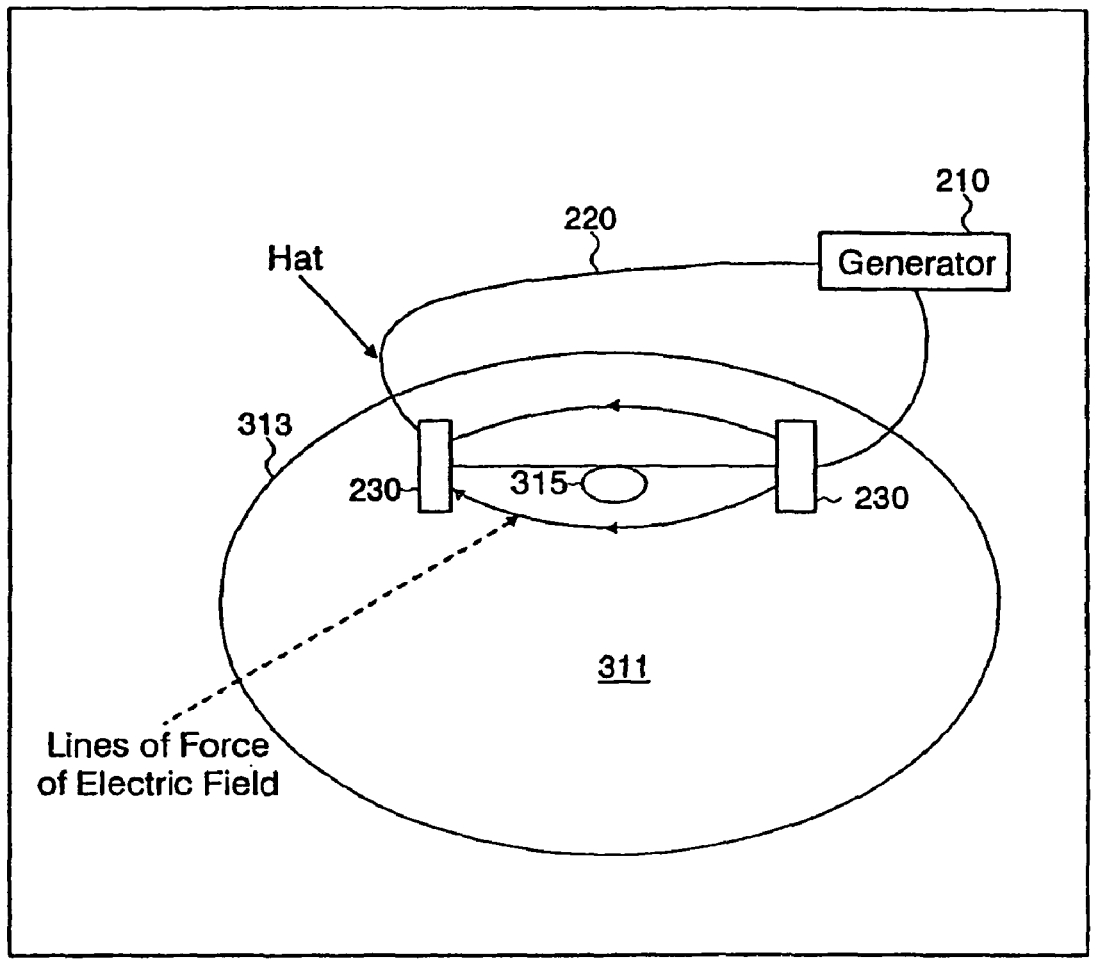
Figure 9:
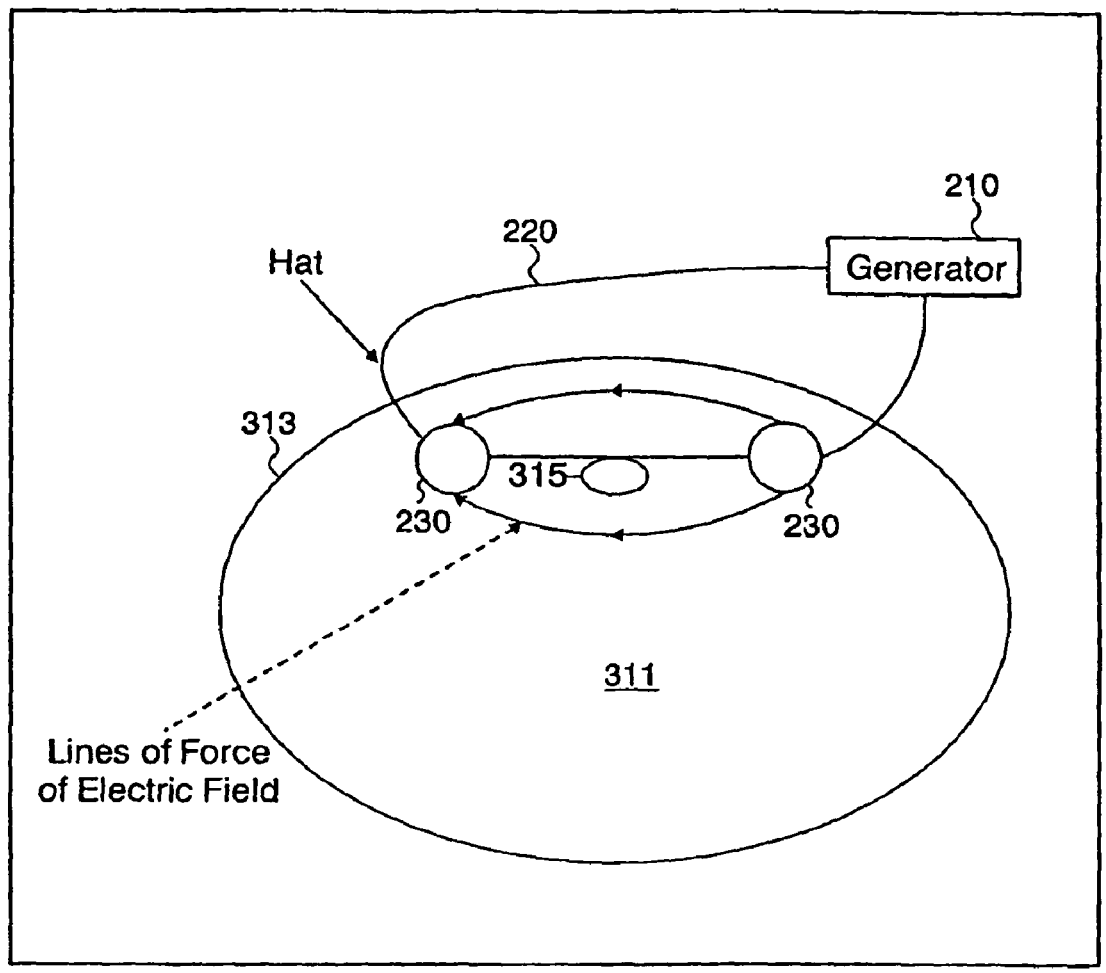

FIGS. 8 and 9 illustrate a second type of treatment using the isolects 230, namely electric field generation by internal isolects 230. A body to which the isolects 230 are implanted is generally indicated at 311 and includes a skin surface 313 and a tumor 315. In this embodiment, the isolects 230 can have the shape of plates, wires or other shapes that can be inserted subcutaneously or a deeper location within the body 311 so as to generate an appropriate field at the target area (tumor 315).

Figure 11:
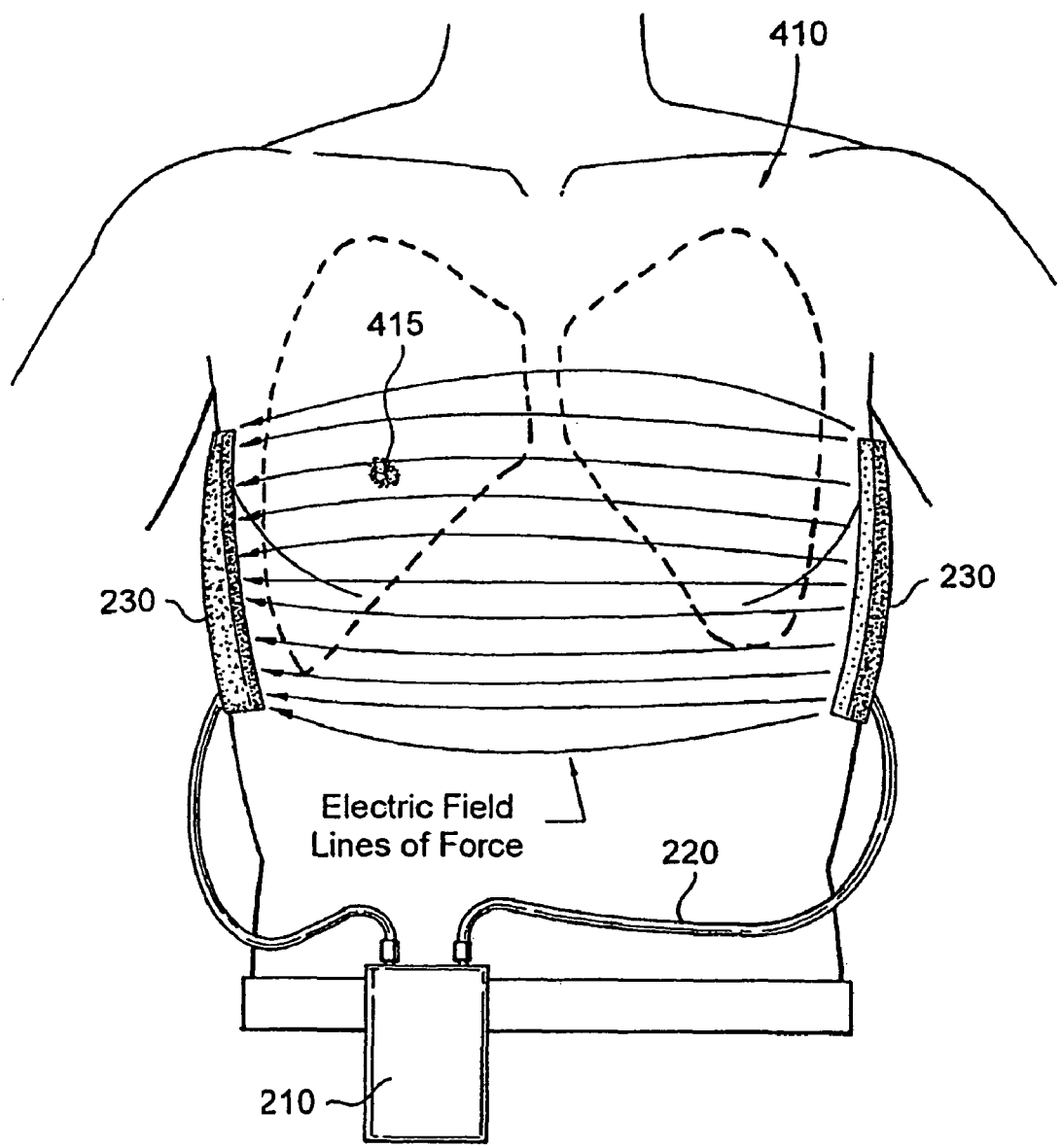
FIG. 11 is a front elevational view in partial cross-section of two insulated electrodes being arranged about a human torso for treatment of a tumor container within the body, e.g., a tumor associated with lung cancer.

It will also be appreciated that the mode of isolects application is not restricted to the above descriptions. In the case of tumors in internal organs, for example, liver, lung, etc., the distance between each member of the pair of isolects 230 can be large. The pairs can even by positioned opposite sides of a torso 410, as illustrated in FIG. 11. The arrangement of the isolects 230 in FIG. 11 is particularly useful for treating a tumor 415 associated with lung cancer or gastro-intestinal tumors. In this embodiment, the electric fields (TC fields) spread in a wide fraction of the body.

In order to avoid overheating of the treated tissues, a selection of materials and field parameters is needed. The isolects insulating material should have minimal dielectric losses at the frequency ranges to be used during the treatment process. This factor can be taken into consideration when choosing the particular frequencies for the treatment. The direct heating of the tissues will most likely be dominated by the heating due to current flow (given by the I*R product). In addition, the isolect (insulated electrode) 230 and its surroundings should be made of materials that facilitate heat losses and its general structure should also facilitate head losses, i.e., minimal structures that block heat dissipation to the surroundings (air) as well as high heat conductivity. Using larger electrodes also minimizes the local sensation of heating, since it spreads the energy that is being transferred into the patient over a larger surface area. Preferably, the heating is minimized to the point where the patient's skin temperature never exceeds about 39° C.

Another way to reduce heating is to apply the field to the tissue being treated intermittently, by applying a field with a duty cycle between about 20% and about 50% instead of using a continuous field. For example, to achieve a duty cycle of 33%, the field would be repetitively switched on for one second, then switched off for two seconds. Preliminary experiments have shown that the efficacy of treatment using a field with a 33% duty cycle is roughly the same as for a field with a duty cycle of 100%. In alternative embodiments, the field could be switched on for one hour then switched off for one hour to achieve a duty cycle of 50%. Of course, switching at a rate of once per hour would not help minimize short-term heating. On the other hand, it could provide the patient with a welcome break from treatment.

Figure 13:
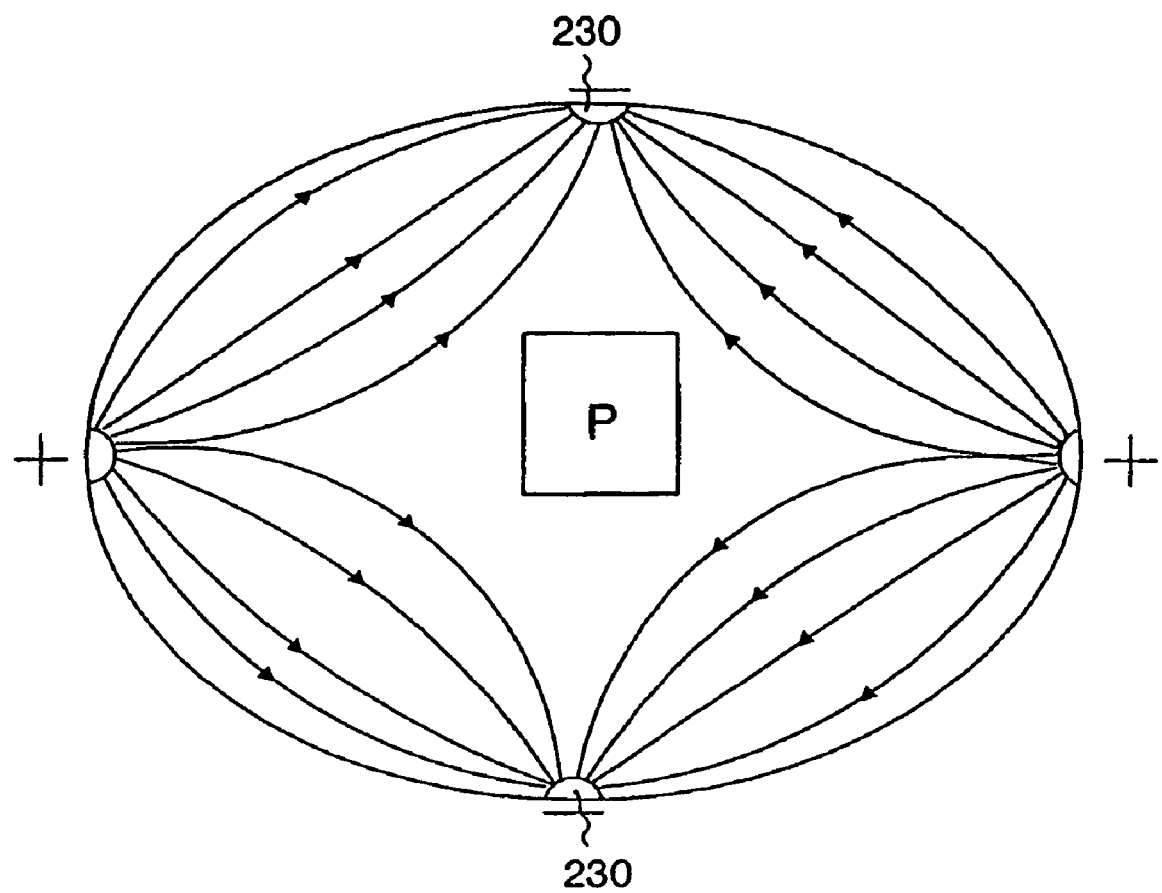
FIG. 13 is a schematic diagram of insulated electrodes that are arranged for focusing the electric field at a desired target while leaving other areas in low field density (i.e., protected areas)

The effectiveness of the treatment can be enhanced by an arrangement of isolects 230 that focuses the field at the desired target while leaving other sensitive areas in low field density (i.e., protected areas). The proper placement of the isolects 230 over the body can be maintained using any number of different techniques, including using a suitable piece of clothing that keeps the isolects at the appropriate positions. FIG. 13 illustrates such an arrangement in which an area labeled as "P" represents a protected area. The lines of field force do not penetrate this protected area and the field there is much smaller than near the isolects 230 where target areas can be located and treated well. In contrast, the field intensity near the four poles is very high.

The following Example serves to illustrate an exemplary application of the present apparatus and application of TC fields; however, this Example is not limiting and does not limit the scope of the present invention in any way.

EXAMPLE

To demonstrate the effectiveness of electric fields having the above described properties (e.g., frequencies between 50 KHz and 500 KHz) in destroying tumor cells, the electric fields were applied to treat mice with malignant melanoma tumors. Two pairs of isolects 230 were positioned over a corresponding pair of malignant melanomas. Only one pair was connected to the generator 210 and 200 KHz alternating electric fields (TC fields) were applied to the tumor for a period of 6 days. One melanoma tumor was not treated so as to permit a comparison between the treated tumor and the non-treated tumor. After treatment for 6 days, the pigmented melanoma tumor remained clearly visible in the non-treated side of the mouse, while, in contrast, no tumor is seen on the treated side of the mouse. The only areas that were visible discernable on the skin were the marks that represented the points of insertion of the isolects 230. The fact that the tumor was eliminated at the treated side was further demonstrated by cutting and inversing the skin so that its inside face was exposed. Such a procedure indicated that the tumor has been substantially, if not completely, eliminated on the treated side of the mouse. The success of the treatment was also further verified by histopathological examination.

The present inventor has thus uncovered that electric fields having particular properties can be used to destroy dividing cells or tumors when the electric fields are applied to using an electronic device. More specifically, these electric fields fall into a special intermediate category, namely bio-effective fields that have no meaningful stimulatory and no thermal effects, and therefore overcome the disadvantages that were associated with the application of conventional electric fields to a body. It will also be appreciated that the present apparatus can further include a device for rotating the TC field relative to the living tissue. For example and according to one embodiment, the alternating electric potential applies to the tissue being treated is rotated relative to the tissue using conventional devices, such as a mechanical device that upon activation, rotates various components of the present system.

Moreover and according to yet another embodiment, the TC fields are applied to different pairs of the insulated electrodes 230 in a consecutive manner. In other words, the generator 210 and the control system thereof can be arranged so that signals are sent at periodic intervals to select pairs of insulated electrodes 230, thereby causing the generation of the TC fields of different directions by these insulated electrodes 230. Because the signals are sent at select times from the generator to the insulated electrodes 230, the TC fields of changing directions are generated consecutively by different insulated electrodes 230. This arrangement has a number of advantages and is provided in view of the fact that the TC fields have maximal effect when they are parallel to the axis of cell division. Since the orientation of cell division is in most cases random, only a fraction of the dividing cells are affected by any given field. Thus, using fields of two or more orientations increases the effectiveness since it increases the chances that more dividing cells are affected by a given TC field.

In vitro experiments have shown that the electric field has the maximum killing effect when the lines of force of the field are oriented generally parallel to the long axis of the hourglass-shaped cell during mitosis (as shown in FIGS. 3A-3C). In one experiment, a much higher proportion of the damaged cells had their axis of division oriented along the field: 56% of the cells oriented at or near 0° with respect to the field were damaged, versus an average of 15% of cells damaged for cells with their long axis oriented at more than 22° with respect to the field.

The inventor has recognized that applying the field in different directions sequentially will increase the overall killing power, because the field orientation that is most effectively in killing dividing cells will be applied to a larger population of the dividing cells. A number of examples for applying the field in different directions are discussed below.

Figure 27A:
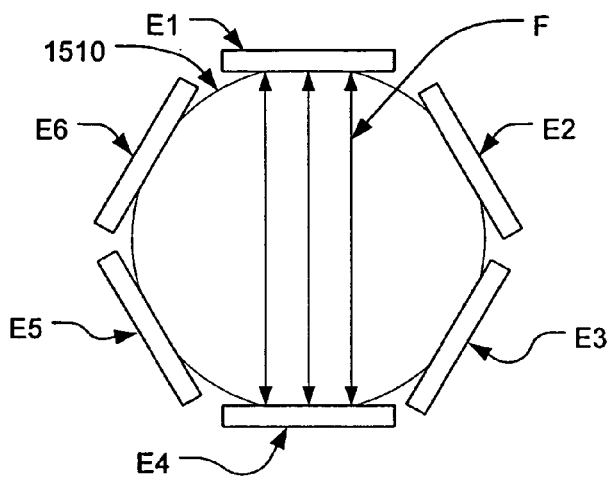
FIGS. 27A-C show a configuration of electrodes that facilitates the application of an electric field in different directions.
Figure 27B:
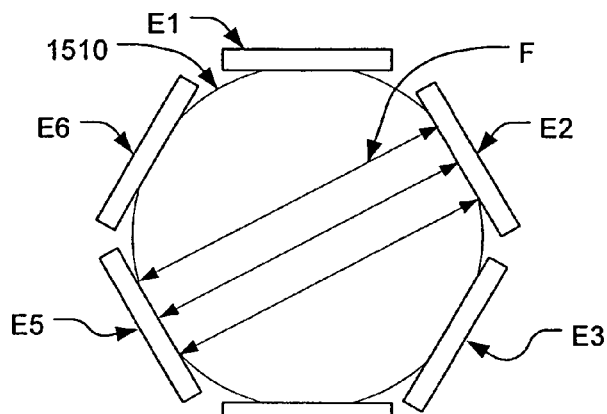
Figure 27C:
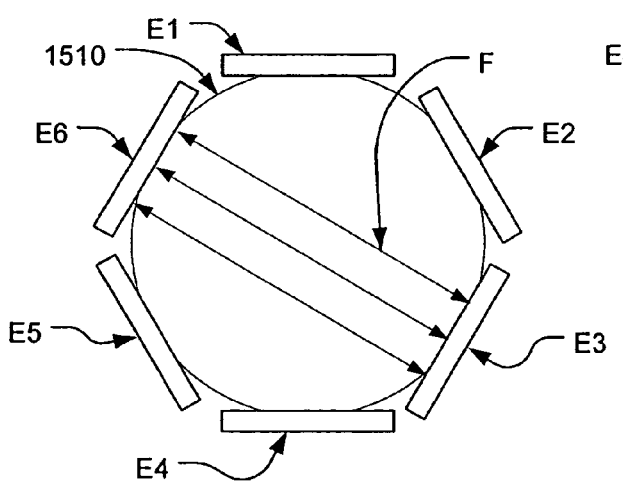

FIGS. 27A, 27B, and 27C show a set of 6 electrodes E1-E6, and how the direction of the field through the target tissue 1510 can be changed by applying the AC signal from the generator 1 (shown in FIG. 1) across different pairs of electrodes. For example, if the AC signal is applied across electrodes E1 and E4, the field lines F would be vertical (as shown in FIG. 27A), and if the signal is applied across electrodes E2 and E5, or across electrodes E3 and E6, the field lines F would be diagonal (as shown in FIGS. 27B and 27C, respectively). Additional field directions can be obtained by applying the AC signal across other pairs of electrodes. For example, a roughly horizontal field could be obtained by applying the signal across electrodes E2 and E6.

In one embodiment, the AC signal is applied between the various pairs of electrodes sequentially. An example of this arrangement is to apply the AC signal across electrodes E1 and E4 for one second, then apply the AC signal across electrodes E2 and E5 for one second, and then apply the AC signal across electrodes E3 and E6 for one second. This three-part sequence is then repeated for the desired period of treatment. Because the efficacy in cell-destruction is strongly dependant on the cell's orientation, cycling the field between the different directions increases the chance that the field will be oriented in a direction that favors cell destruction at least part of the time.

Of course, the 6 electrode configuration shown in FIGS. 27A-C is just one of many possible arrangement of multiple electrodes, and many other configurations of three or more electrodes could be used based on the same principles.

Figure 28:
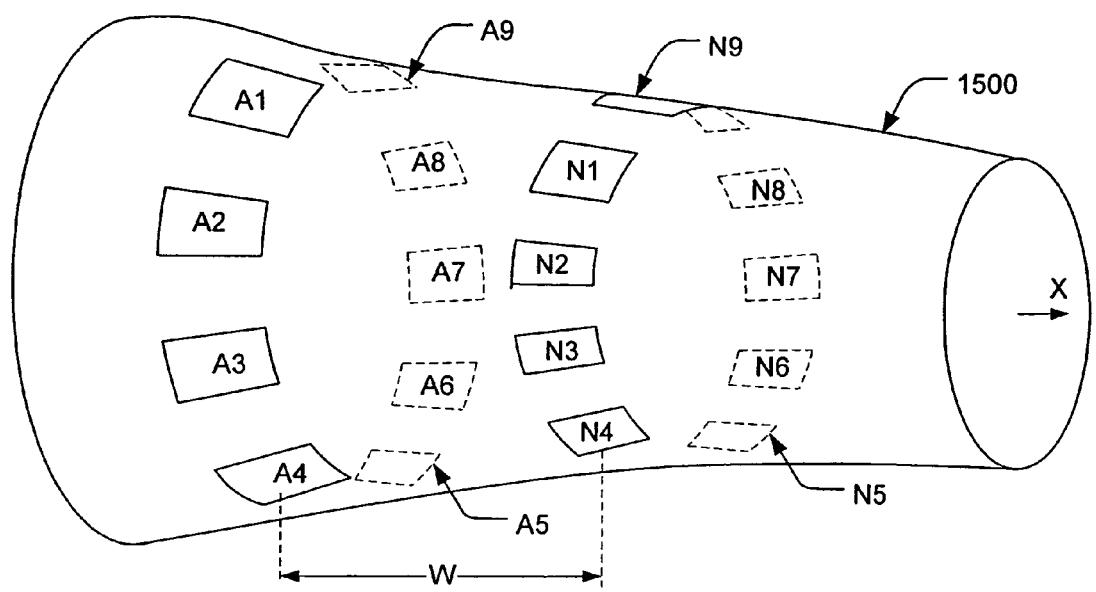
FIG. 28 shows a three-dimensional arrangement of electrodes about a body part that facilitates the application of an electric field in different directions.

Application of the field in different directions sequentially is not limited to two dimensional embodiments, and FIG. 28 shows how the sequential application of signals across different sets of electrodes can be extended to three dimensions. A first array of electrodes A1-A9 is arranged around body part 1500, and a last array of electrodes N1-N9 is arranged around the body part 1500 a distance W away from the first array. Additional arrays of electrodes may optionally be added between the first array and the last array, but these additional arrays are not illustrated for clarity (so as not to obscure the electrodes A5-A9 and B5-B8 on the back of the body part 1500).

As in the FIG. 27 embodiment, the direction of the field through the target tissue can be changed by applying the AC signal from the generator 1 (shown in FIG. 1) across different pairs of electrodes. For example, applying the AC signal between electrodes A2 and A7 would result in a field in a front-to-back direction between those two electrodes, and applying the AC signal between electrodes A5 and A9 would result in a roughly vertical field between those two electrodes. Similarly, applying the AC signal across electrodes A2 and N7 would generate diagonal field lines in one direction through the body part 1500, and applying the AC signal across electrodes A2 and B7 would generate diagonal field lines in another direction through the body part.

Using a three-dimensional array of electrodes also makes it possible to energize multiple pairs of electrodes simultaneously to induce fields in the desired directions. For example, if suitable switching is provided so that electrodes A2 through N2 are all connected to one terminal of the generator, and so that electrodes A7 through N7 are all connected to the other terminal of the generator, the resulting field would be a sheet that extends in a front-to-back direction for the entire width W. After the front-to-back field is maintained for a suitable duration (e.g., one second), the switching system (not shown) is reconfigured to connect electrodes A3 through N3 to one terminal of the generator, and electrodes A8 through N8 to the other terminal of the generator. This results in a sheet-shaped field that is rotated about the Z axis by about 40° with respect to the initial field direction. After the field is maintained in this direction for a suitable duration (e.g., one second), the next set of electrodes is activated to rotate the field an additional 40° to its next position. This continues until the field returns to its initial position, at which point the whole process is repeated.

Optionally, the rotating sheet-shaped field may be added (sequentially in time) to the diagonal fields described above, to better target cells that are oriented along those diagonal axes.

Because the electric field is a vector, the signals may optionally be applied to combinations of electrodes simultaneously in order to form a desired resultant vector. For example, a field that is rotated about the X axis by 20° with respect to the initial position can be obtained by switching electrodes A2 through N2 and A3 through N3 all to one terminal of the generator, and switching electrodes A7 through N7 and A8 through N8 all to the other terminal of the generator. Applying the signals to other combinations of electrodes will result in fields in other directions, as will be appreciated by persons skilled in the relevant arts. If appropriate computer control of the voltages is implemented, the field's direction can even be swept through space in a continuous (i.e., smooth) manner, as opposed to the stepwise manner described above.

Figure 29A:
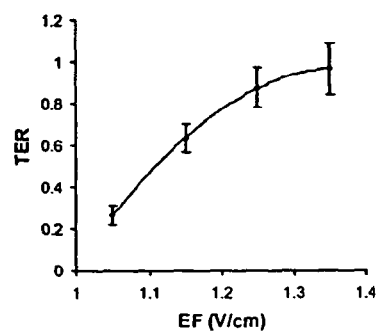
FIGS. 29A and 29B are graphs of the efficiency of the cell destruction process as a function of field strength for melanoma and glioma cells, respectively.
Figure 29B:
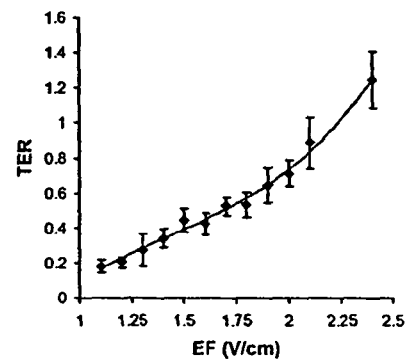

FIGS. 29A and 29B depict the results of in vitro experiments that show how the killing power of the applied field against dividing cells is a function of the field strength. In the FIG. 29A experiment, B16F1 melanoma cells were subjected to a 100 kHz AC field at different field strengths, for a period of 24 hours at each strength. In the FIG. 29B experiment, F-98 glioma cells were subjected to a 200 kHz AC field at different field strengths, for a period of 24 hours at each strength. In both of these figures, the strength of the field (EF) is measured in Volts per cm. The magnitude of the killing effect is expressed in terms of TER, which is which is the ratio of the decrease in the growth rate of treated cells (GRT) compared with the growth rate of control cells (GRc).

$$TER = \frac{GR_C - GR_T}{GR_C}$$

The experimental results show that the inhibitory effect of the applied field on proliferation increases with intensity in both the melanoma and the glioma cells. Complete proliferation arrest (TER=1) is seen at 1.35 and 2.25 V/cm in melanoma and glioma cells, respectively.

Figure 30A:
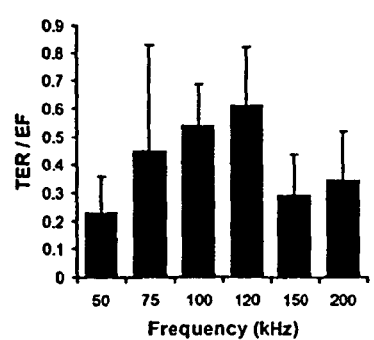
FIGS. 30A and 30B are graphs that show how the cell destruction efficiency is a function of the frequency of the applied field for melanoma and glioma cells, respectively.
Figure 30B:
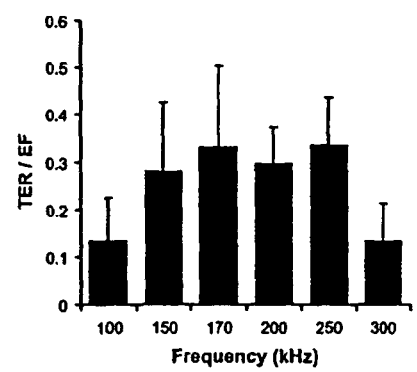

FIGS. 30A and 30B depict the results of in vitro experiments that show how the killing power of the applied field is a function of the frequency of the field. In the experiments, B16F1 melanoma cells (FIG. 30A) and F-98 glioma cells (FIG. 30B) were subjected to fields with different frequencies, for a period of 24 hours at each frequency. FIGS. 30A and 30B show the change in the growth rate, normalized to the field intensity (TER/EF). Data are shown as mean+SE. In FIG. 30A, a window effect is seen with maximal inhibition at 120 kHz in melanoma cells. In FIG. 30B, two peaks are seen at 170 and 250 kHz. Thus, if only one frequency is available during an entire course of treatment, a field with a frequency of about 120 kHz would be appropriate for destroying melanoma cells, and a field with a frequency on the order of 200 kHz would be appropriate for destroying glioma cells.

Not all the cells of any given type will have the exact same size. Instead, the cells will have a distribution of sizes, with some cells being smaller and some cells being larger. It is believed that the best frequency for damaging a particular cell is related to the physical characteristics (e.g., the size) of that particular cell. Thus, to best damage a population of cells with a distribution of sizes, it can be advantageous to apply a distribution of different frequencies to the population, where the selection of frequencies is optimized based on the expected size distribution of the target cells. For example, the data on FIG. 30B indicates that using two frequencies of 170 kHz and 250 kHz to destroy a population of glioma cells would be more effective than using a single frequency of 200 kHz.

Note that the optimal field strengths and frequencies discussed herein were obtained based on in vitro experiments, and that the corresponding parameters for in vivo applications may be obtained by performing similar experiments in vivo. It is possible that relevant characteristics of the cell itself (such as size and/or shape) or interactions with the cell's surroundings may result in a different set of optimal frequencies and/or field strengths for in vivo applications.

When more than one frequency is used, the various frequencies may be applied sequentially in time. For example, in the case of glioma, field frequencies of 100, 150, 170, 200, 250, and 300 kHz may be applied during the first, second, third, fourth, fifth, and sixth minutes of treatment, respectively. That cycle of frequencies would then repeat during each successive six minutes of treatment. Alternatively, the frequency of the field may be swept in a stepless manner from 100 to 300 kHz.

Figure 31A:
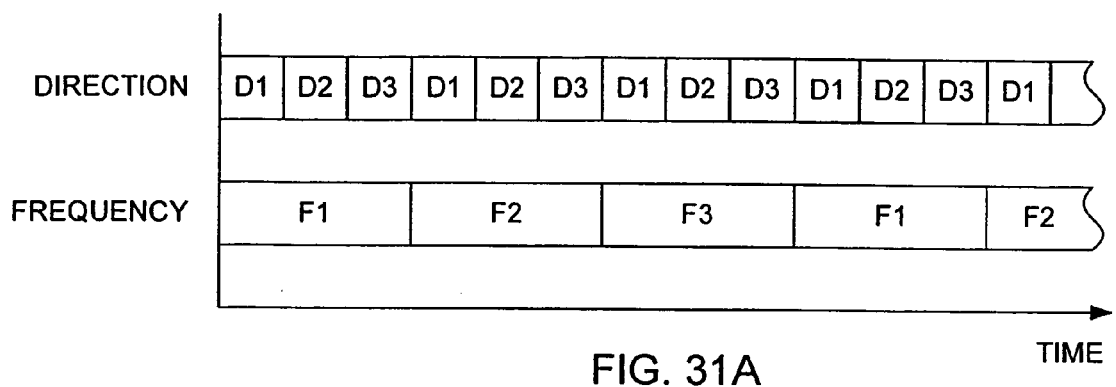
FIG. 31A is a graphical representation of the sequential application of a plurality of frequencies in a plurality of directions.
Figure 31B:
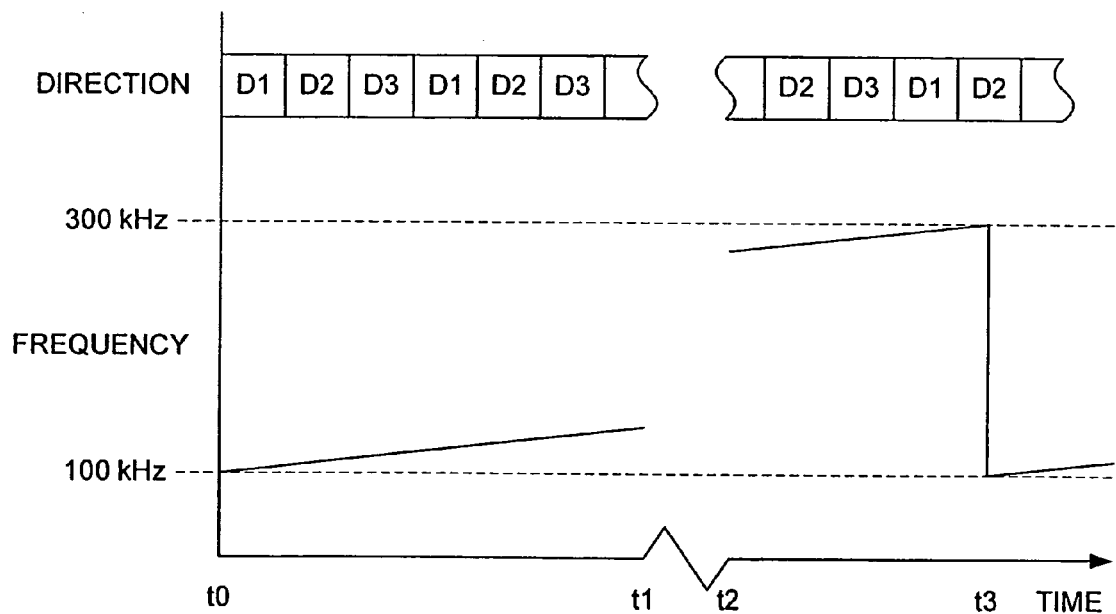
FIG. 31B is a graphical representation of the sequential application of a sweeping frequency in a plurality of directions.

Optionally, this frequency cycling may be combined with the directional cycling described above. FIG. 31A is an example of such a combination using three directions (D1, D2, and D3) and three frequencies (F1, F2, and F3). Of course, the same scheme can be extended to any other number of directions and/or frequencies. FIG. 31B is an example of such a combination using three directions (D1, D2, and D3), sweeping the frequency from 100 kHz to 300 kHz. Note that the break in the time axis between t1 and t2 provides the needed time for the sweeping frequency to rise to just under 300 kHz. The frequency sweeping (or stepping) may be synchronized with directional changes, as shown in FIG. 31A. Alternatively, the frequency sweeping (or stepping) may be asynchronous with respect to the directional changes, as shown in FIG. 31B.

In an alternative embodiment, a signal that contains two or more frequencies components simultaneously (e.g., 170 kHz and 250 kHz) is applied to the electrodes to treat a populations of cells that have a distribution of sizes. The various signals will add by superposition to create a field that includes all of the applied frequency components.

Figure 14:
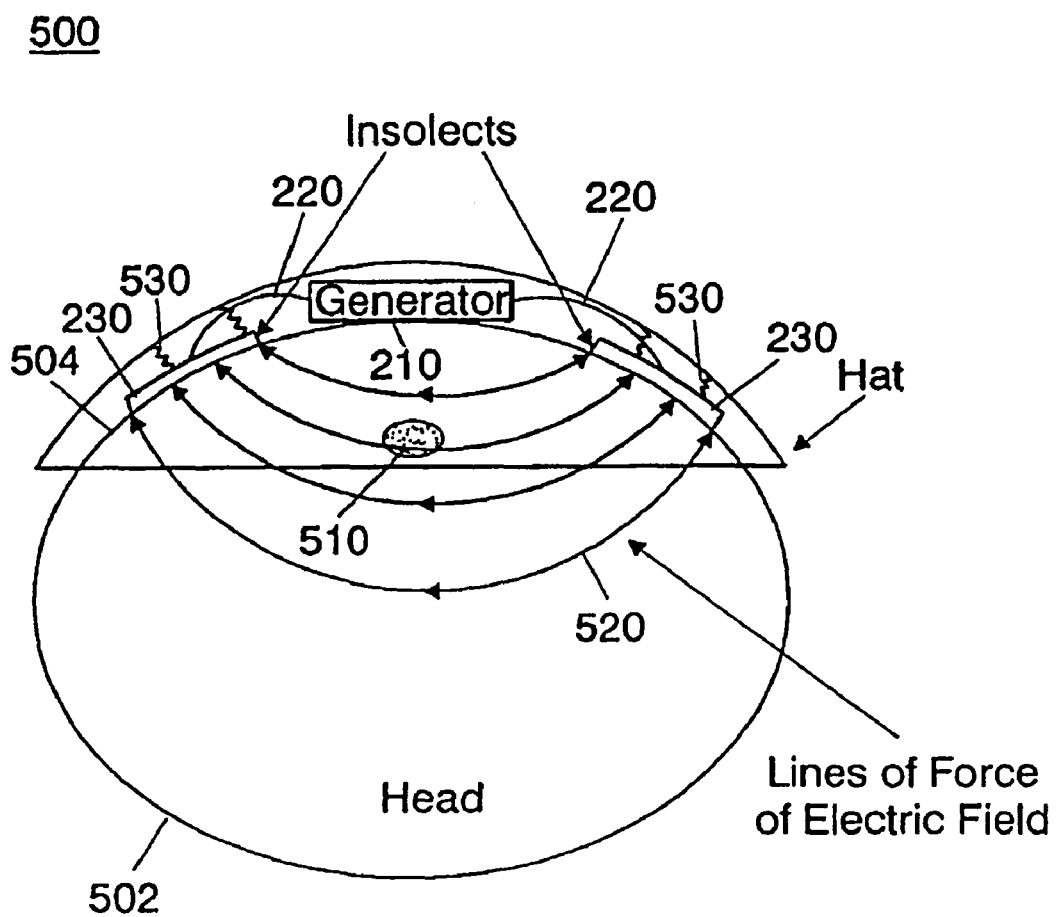

Turning now to FIG. 14 in which an article of clothing 500 according to one exemplary embodiment is illustrated. More specifically, the article of clothing 500 is in the form of a hat or cap or other type of clothing designed for placement on a head of a person. For purposes of illustration, a head 502 is shown with the hat 500 being placed thereon and against a skin surface 504 of the head 502. An intra-cranial tumor or the like 510 is shown as being formed within the head 502 underneath the skin surface 504 thereof. The hat 500 is therefore intended for placement on the head 502 of a person who has a tumor 510 or the like.

Unlike the various embodiments illustrated in FIGS. 1-13 where the insulated electrodes 230 are arranged in a more or less planar arrangement since they are placed either on a skin surface or embedded within the body underneath it, the insulated electrodes 230 in this embodiment are specifically contoured and arranged for a specific application. The treatment of intra-cranial tumors or other lesions or the like typically requires a treatment that is of a relatively long duration, e.g., days to weeks, and therefore, it is desirable to provide as much comfort as possible to the patient. The hat 500 is specifically designed to provide comfort during the lengthy treatment process while not jeopardizing the effectiveness of the treatment.

According to one exemplary embodiment, the hat 500 includes a predetermined number of insulated electrodes 230 that are preferably positioned so as to produce the optimal TC fields at the location of the tumor 510. The lines of force of the TC field are generally indicated at 520. As can be seen in FIG. 14, the tumor 510 is positioned within these lines of force 520. As will be described in greater detail hereinafter, the insulated electrodes 230 are positioned within the hat 500 such that a portion or surface thereof is free to contact the skin surface 504 of the head 502. In other words, when the patient wears the hat 500, the insulated electrodes 230 are placed in contact with the skin surface 504 of the head 502 in positions that are selected so that the TC fields generated thereby are focused at the tumor 510 while leaving surrounding areas in low density. Typically, hair on the head 502 is shaved in selected areas to permit better contact between the insulated electrodes 230 and the skin surface 504; however, this is not critical.

The hat 500 preferably includes a mechanism 530 that applies a force to the insulated electrodes 230 so that they are pressed against the skin surface 502. For example, the mechanism 530 can be of a biasing type that applies a biasing force to the insulated electrodes 230 to cause the insulated electrodes 230 to be directed outwardly away from the hat 500. Thus, when the patient places the hat 500 on his/her head 502, the insulated electrodes 230 are pressed against the skin surface 504 by the mechanism 530. The mechanism 530 can slightly recoil to provide a comfortable fit between the insulated electrodes 230 and the head 502. In one exemplary embodiment, the mechanism 530 is a spring based device that is disposed within the hat 500 and has one section that is coupled to and applies a force against the insulated electrodes 230.

As with the prior embodiments, the insulated electrodes 230 are coupled to the generator 210 by means of conductors 220. The generator 210 can be either disposed within the hat 500 itself so as to provide a compact, self-sufficient, independent system or the generator 210 can be disposed external to the hat 500 with the conductors 220 exiting the hat 500 through openings or the like and then running to the generator 210. When the generator 210 is disposed external to the hat 500, it will be appreciated that the generator 210 can be located in any number of different locations, some of which are in close proximity to the hat 500 itself, while others can be further away from the hat 500. For example, the generator 210 can be disposed within a carrying bag or the like (e.g., a bag that extends around the patient's waist) which is worn by the patient or it can be strapped to an extremity or around the torso of the patient. The generator 210 can also be disposed in a protective case that is secured to or carried by another article of clothing that is worn by the patient. For example, the protective case can be inserted into a pocket of a sweater, etc. FIG. 14 illustrates an embodiment where the generator 210 is incorporated directly into the hat 500.

Figure 15:
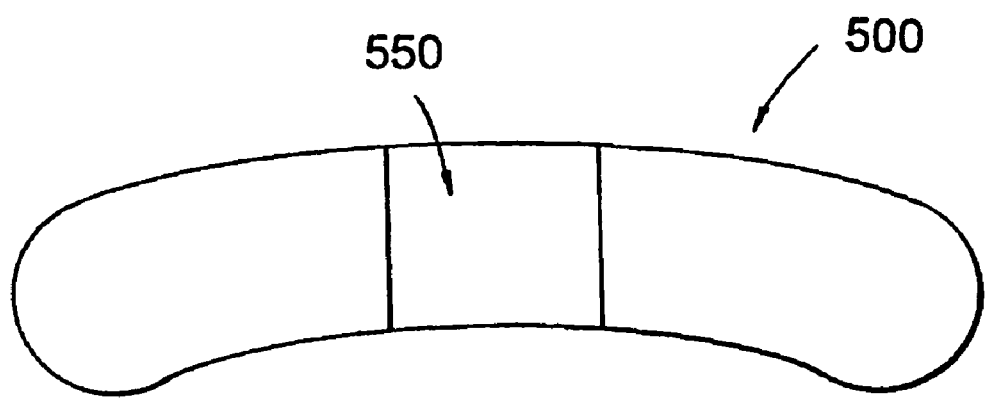
FIG. 15 is a partial section of a hat according to an exemplary embodiment having a recessed section for receiving one or more insulated electrodes.
Figure 16:
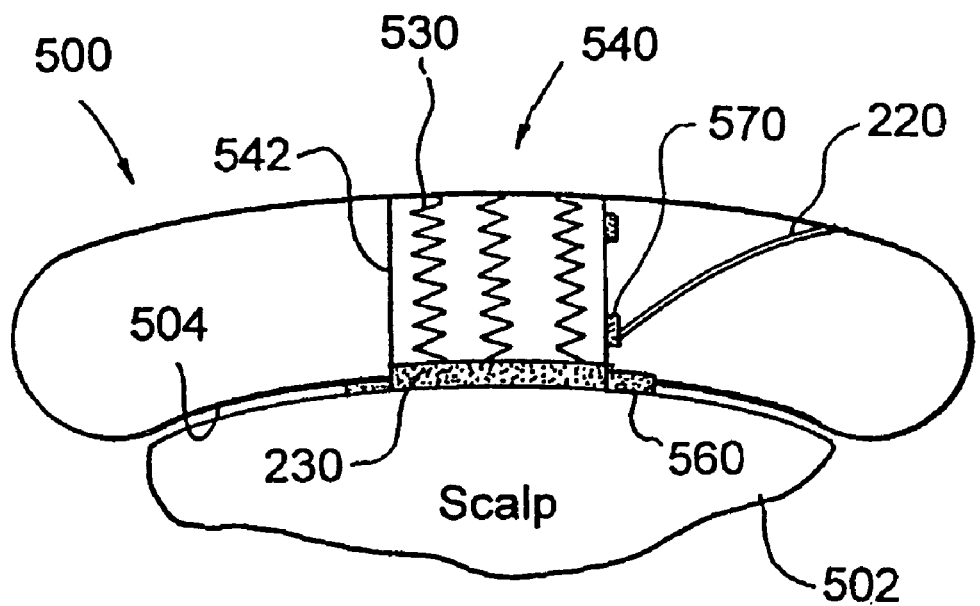
FIG. 16 is a cross-sectional view of the hat of FIG. 15 placed on a head and illustrating a biasing mechanism for applying a force to the insulated electrode to ensure the insulated electrode remains in contact against the head.

Turning now to FIGS. 15 and 16, in one exemplary embodiment, a number of insulated electrodes 230 along with the mechanism 530 are preferably formed as an independent unit, generally indicated at 540, that can be inserted into the hat 500 and electrically connected to the generator (not shown) via the conductors (not shown). By providing these members in the form of an independent unit, the patient can easily insert and/or remove the units 540 from the hat 500 when they may need cleaning, servicing and/or replacement.

In this embodiment, the hat 500 is constructed to include select areas 550 that are formed in the hat 500 to receive and hold the units 540. For example and as illustrated in FIG. 15, each area 550 is in the form of an opening (pore) that is formed within the hat 500. The unit 540 has a body 542 and includes the mechanism 530 and one or more insulated electrodes 230. The mechanism 530 is arranged within the unit 540 so that a portion thereof (e.g., one end thereof) is in contact with a face of each insulated electrode 230 such that the mechanism 530 applies a biasing force against the face of the insulated electrode 230. Once the unit 540 is received within the opening 550, it can be securely retained therein using any number of conventional techniques, including the use of an adhesive material or by using mechanical means. For example, the hat 500 can include pivotable clip members that pivot between an open position in which the opening 550 is free and a closed position in which the pivotable clip members engage portions (e.g., peripheral edges) of the insulated electrodes to retain and hold the insulated electrodes 230 in place. To remove the insulated electrodes 230, the pivotable clip members are moved to the open position. In the embodiment illustrated in FIG. 16, the insulated electrodes 230 are retained within the openings 550 by an adhesive element 560 which in one embodiment is a two sided self-adhesive rim member that extends around the periphery of the insulated electrode 230. In other words, a protective cover of one side of the adhesive rim 560 is removed and it is applied around the periphery of the exposed face of the insulated electrode 230, thereby securely attaching the adhesive rim 560 to the hat 500 and then the other side of the adhesive rim 560 is removed for application to the skin surface 504 in desired locations for positioning and securing the insulated electrode 230 to the head 502 with the tumor being positioned relative thereto for optimization of the TC fields. Since one side of the adhesive rim 560 is in contact with and secured to the skin surface 540, this is why it is desirable for the head 502 to be shaved so that the adhesive rim 560 can be placed flushly against the skin surface 540.

The adhesive rim 560 is designed to securely attach the unit 540 within the opening 550 in a manner that permits the unit 540 to be easily removed from the hat 500 when necessary and then replaced with another unit 540 or with the same unit 540. As previously mentioned, the unit 540 includes the biasing mechanism 530 for pressing the insulated electrode 230 against the skin surface 504 when the hat 500 is worn. The unit 540 can be constructed so that side opposite the insulated electrode 230 is a support surface formed of a rigid material, such as plastic, so that the biasing mechanism 530 (e.g., a spring) can be compressed therewith under the application of force and when the spring 530 is in a relaxed state, the spring 530 remains in contact with the support surface and the applies a biasing force at its other end against the insulated electrode 230. The biasing mechanism 530 (e.g., spring) preferably has a contour corresponding to the skin surface 504 so that the insulated electrode 230 has a force applied thereto to permit the insulated electrode 230 to have a contour complementary to the skin surface 504, thereby permitting the two to seat flushly against one another. While the mechanism 530 can be a spring, there are a number of other embodiments that can be used instead of a spring. For example, the mechanism 530 can be in the form of an elastic material, such as a foam rubber, a foam plastic, or a layer containing air bubbles, etc.

The unit 540 has an electric connector 570 that can be hooked up to a corresponding electric connector, such as a conductor 220, that is disposed within the hat 500. The conductor 220 connects at one end to the unit 540 and at the other end is connected to the generator 210. The generator 210 can be incorporated directly into the hat 500 or the generator 210 can be positioned separately (remotely) on the patient or on a bedside support, etc.

As previously discussed, a coupling agent, such as a conductive gel, is preferably used to ensure that an effective conductive environment is provided between the insulated electrode 230 and the skin surface 504. Suitable gel materials have been disclosed hereinbefore in the discussion of earlier embodiments. The coupling agent is disposed on the insulated electrode 230 and preferably, a uniform layer of the agent is provided along the surface of the electrode 230. One of the reasons that the units 540 need replacement at periodic times is that the coupling agent needs to be replaced and/or replenished. In other words, after a predetermined time period or after a number of uses, the patient removes the units 540 so that the coupling agent can be applied again to the electrode 230.

Figure 17:
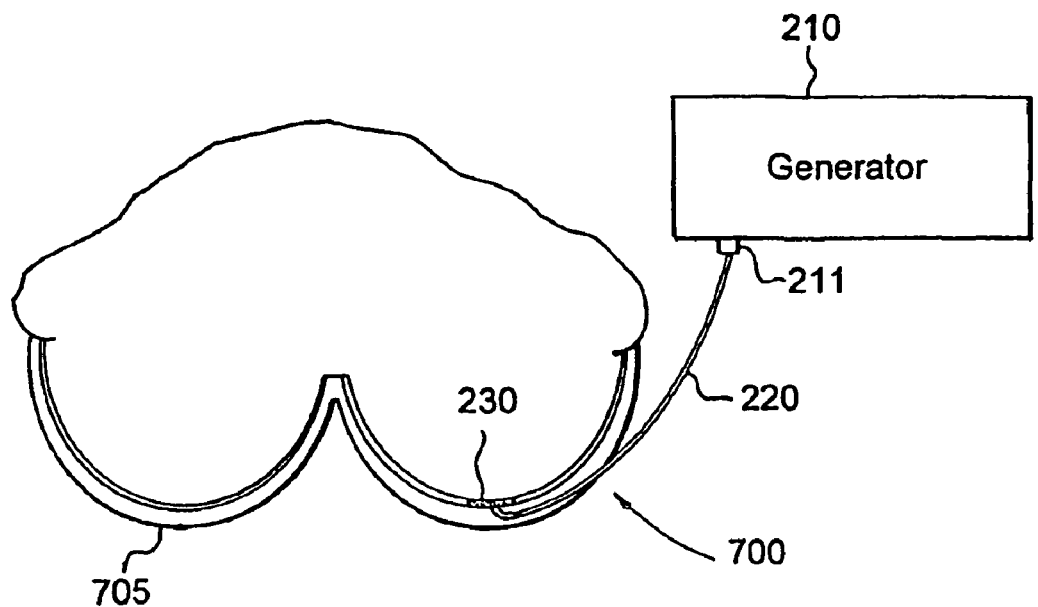
Figure 18:
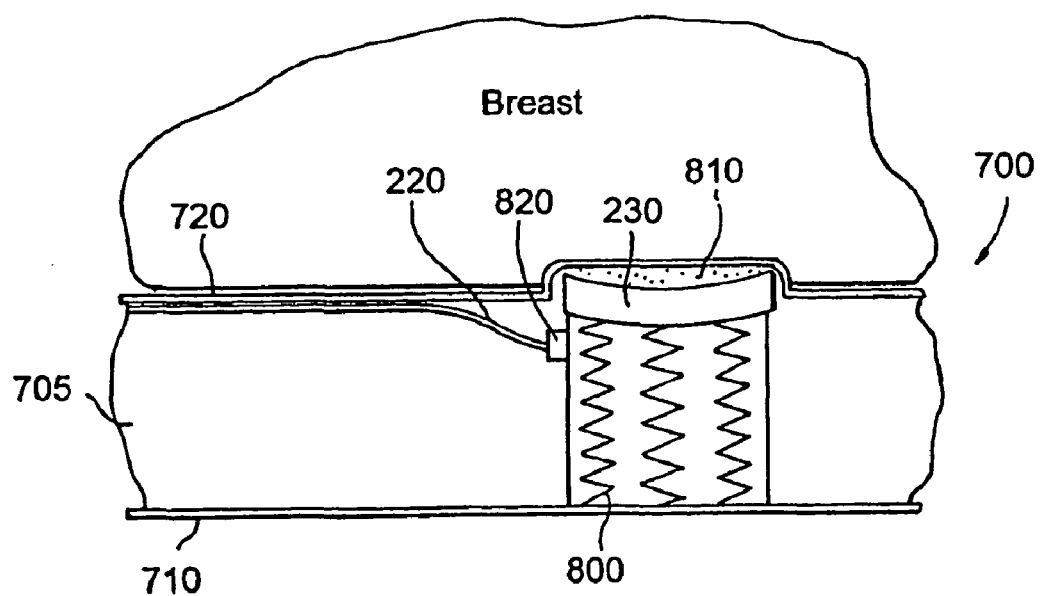
FIG. 18 is a cross-sectional view of a section of the article of clothing of FIG. 17 illustrating a biasing mechanism for biasing the insulated electrode in direction to ensure the insulated electrode is placed proximate to a skin surface where treatment is desired.

FIGS. 17 and 18 illustrate another article of clothing which has the insulated electrodes 230 incorporated as part thereof. More specifically, a bra or the like 700 is illustrated and includes a body that is formed of a traditional bra material, generally indicated at 705, to provide shape, support and comfort to the wearer. The bra 700 also includes a fabric support layer 710 on one side thereof. The support layer 710 is preferably formed of a suitable fabric material that is constructed to provide necessary and desired support to the bra 700.

Similar to the other embodiments, the bra 700 includes one or more insulated electrodes 230 disposed within the bra material 705. The one or more insulated electrodes are disposed along an inner surface of the bra 700 opposite the support 710 and are intended to be placed proximate to a tumor or the like that is located within one breast or in the immediately surrounding area. As with the previous embodiment, the insulated electrodes 230 in this embodiment are specifically constructed and configured for application to a breast or the immediate area. Thus, the insulated electrodes 230 used in this application do not have a planar surface construction but rather have an arcuate shape that is complementary to the general curvature found in a typical breast.

A lining 720 is disposed across the insulated electrodes 230 so as to assist in retaining the insulated electrodes in their desired locations along the inner surface for placement against the breast itself. The lining 720 can be formed of any number of thin materials that are comfortable to wear against one's skin and in one exemplary embodiment, the lining 720 is formed of a fabric material.

The bra 700 also preferably includes a biasing mechanism 800 as in some of the earlier embodiments. The biasing mechanism 800 is disposed within the bra material 705 and extends from the support 710 to the insulated electrode 230 and applies a biasing force to the insulated electrode 230 so that the electrode 230 is pressed against the breast. This ensures that the insulated electrode 230 remains in contact with the skin surface as opposed to lifting away from the skin surface, thereby creating a gap that results in a less effective treatment since the gap diminishes the efficiency of the TC fields. The biasing mechanism 800 can be in the form of a spring arrangement or it can be an elastic material that applies the desired biasing force to the insulated electrodes 230 so as to press the insulated electrodes 230 into the breast. In the relaxed position, the biasing mechanism 800 applies a force against the insulated electrodes 230 and when the patient places the bra 700 on their body, the insulated electrodes 230 are placed against the breast which itself applies a force that counters the biasing force, thereby resulting in the insulated electrodes 230 being pressed against the patient's breast. In the exemplary embodiment that is illustrated, the biasing mechanism 800 is in the form of springs that are disposed within the bra material 705.

A conductive gel 810 can be provided on the insulated electrode 230 between the electrode and the lining 720. The conductive gel layer 810 is formed of materials that have been previously described herein for performing the functions described above.

An electric connector 820 is provided as part of the insulated electrode 230 and electrically connects to the conductor 220 at one end thereof, with the other end of the conductor 220 being electrically connected to the generator 210. In this embodiment, the conductor 220 runs within the bra material 705 to a location where an opening is formed in the bra 700. The conductor 220 extends through this opening and is routed to the generator 210, which in this embodiment is disposed in a location remote from the bra 700. It will also be appreciated that the generator 210 can be disposed within the bra 700 itself in another embodiment. For example, the bra 700 can have a compartment formed therein which is configured to receive and hold the generator 210 in place as the patient wears the bra 700. In this arrangement, the compartment can be covered with a releasable strap that can open and close to permit the generator 210 to be inserted therein or removed therefrom. The strap can be formed of the same material that is used to construct the bra 700 or it can be formed of some other type of material. The strap can be releasably attached to the surrounding bra body by fastening means, such as a hook and loop material, thereby permitting the patient to easily open the compartment by separating the hook and loop elements to gain access to the compartment for either inserting or removing the generator 210.

The generator 210 also has a connector 211 for electrical connection to the conductor 220 and this permits the generator 210 to be electrically connected to the insulated electrodes 230.

As with the other embodiments, the insulated electrodes 230 are arranged in the bra 700 to focus the electric field (TC fields) on the desired target (e.g., a tumor). It will be appreciated that the location of the insulated electrodes 230 within the bra 700 will vary depending upon the location of the tumor. In other words, after the tumor has been located, the physician will then devise an arrangement of insulated electrodes 230 and the bra 700 is constructed in view of this arrangement so as to optimize the effects of the TC fields on the target area (tumor). The number and position of the insulated electrodes 230 will therefore depend upon the precise location of the tumor or other target area that is being treated. Because the location of the insulated electrodes 230 on the bra 700 can vary depending upon the precise application, the exact size and shape of the insulated electrodes 230 can likewise vary. For example, if the insulated electrodes 230 are placed on the bottom section of the bra 700 as opposed to a more central location, the insulated electrodes 230 will have different shapes since the shape of the breast (as well as the bra) differs in these areas.

Figure 19:
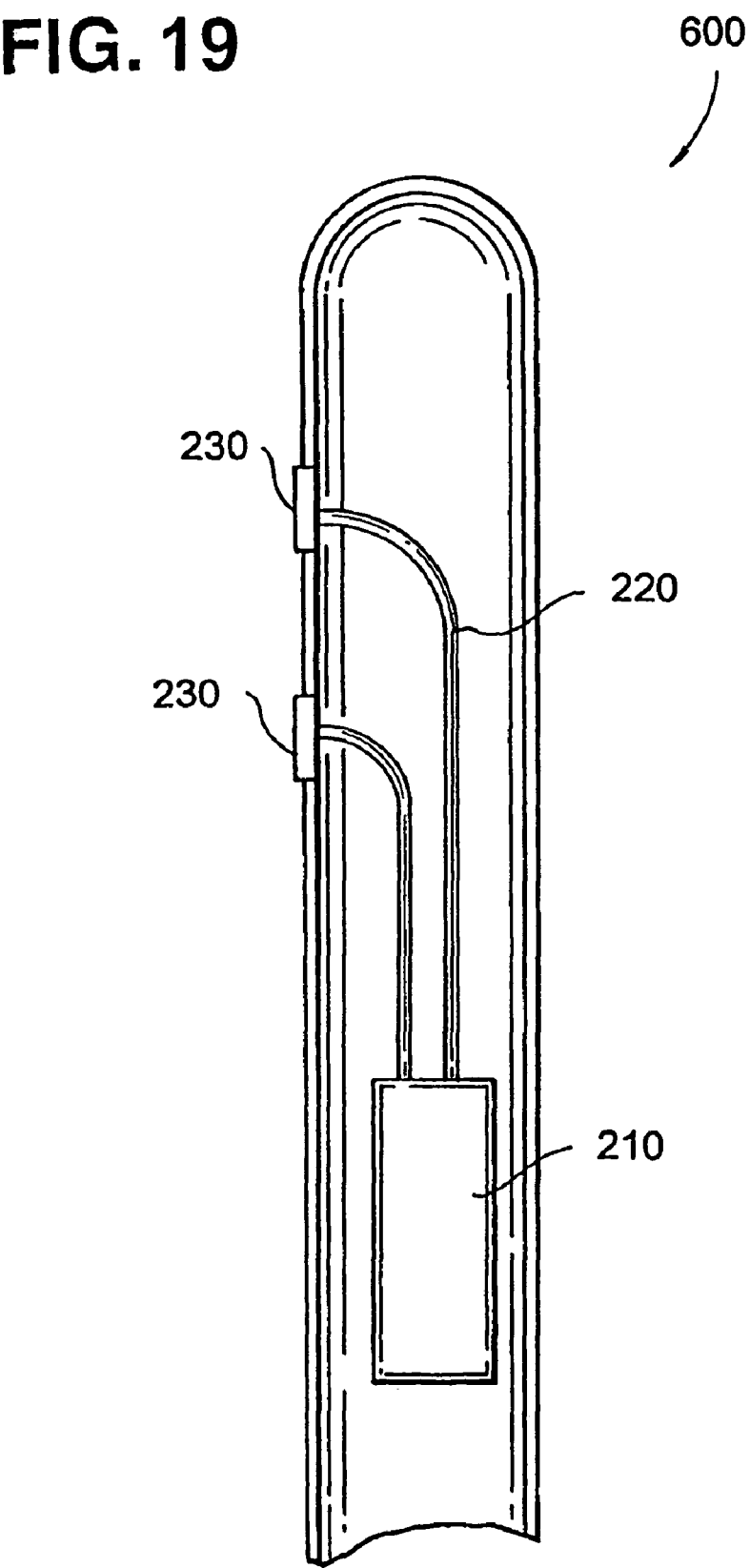

FIG. 19 illustrates yet another embodiment in which the insulated electrodes 230 are in the form of internal electrodes that are incorporated into in the form of a probe or catheter 600 that is configured to enter the body through a natural pathway, such as the urethra, vagina, etc. In this embodiment, the insulated electrodes 230 are disposed on an outer surface of the probe 600 and along a length thereof. The conductors 220 are electrically connected to the electrodes 230 and run within the body of the probe 600 to the generator 210 which can be disposed within the probe body or the generator 210 can be disposed independent of the probe 600 in a remote location, such as on the patient or at some other location close to the patient.

Alternatively, the probe 600 can be configured to penetrate the skin surface or other tissues to reach an internal target that lies within the body. For example, the probe 600 can penetrate the skin surface and then be positioned adjacent to or proximate to a tumor that is located within the body.

In these embodiments, the probe 600 is inserted through the natural pathway and then is positioned in a desired location so that the insulated electrodes 230 are disposed near the target area (i.e., the tumor). The generator 210 is then activated to cause the insulated electrodes 230 to generate the TC fields which are applied to the tumor for a predetermined length of time. It will be appreciated that the illustrated probe 600 is merely exemplary in nature and that the probe 600 can have other shapes and configurations so long as they can perform the intended function. Preferably, the conductors (e.g., wires) leading from the insulated electrodes 230 to the generator 210 are twisted or shielded so as not to generate a field along the shaft.

It will further be appreciated that the probes can contain only one insulated electrode while the other can be positioned on the body surface. This external electrode should be larger or consist of numerous electrodes so as to result in low lines of force-current density so as not to affect the untreated areas. In fact, the placing of electrodes should be designed to minimize the field at potentially sensitive areas. Optionally, the external electrodes may be held against the skin surface by a vacuum force (e.g., suction).

Figure 20:
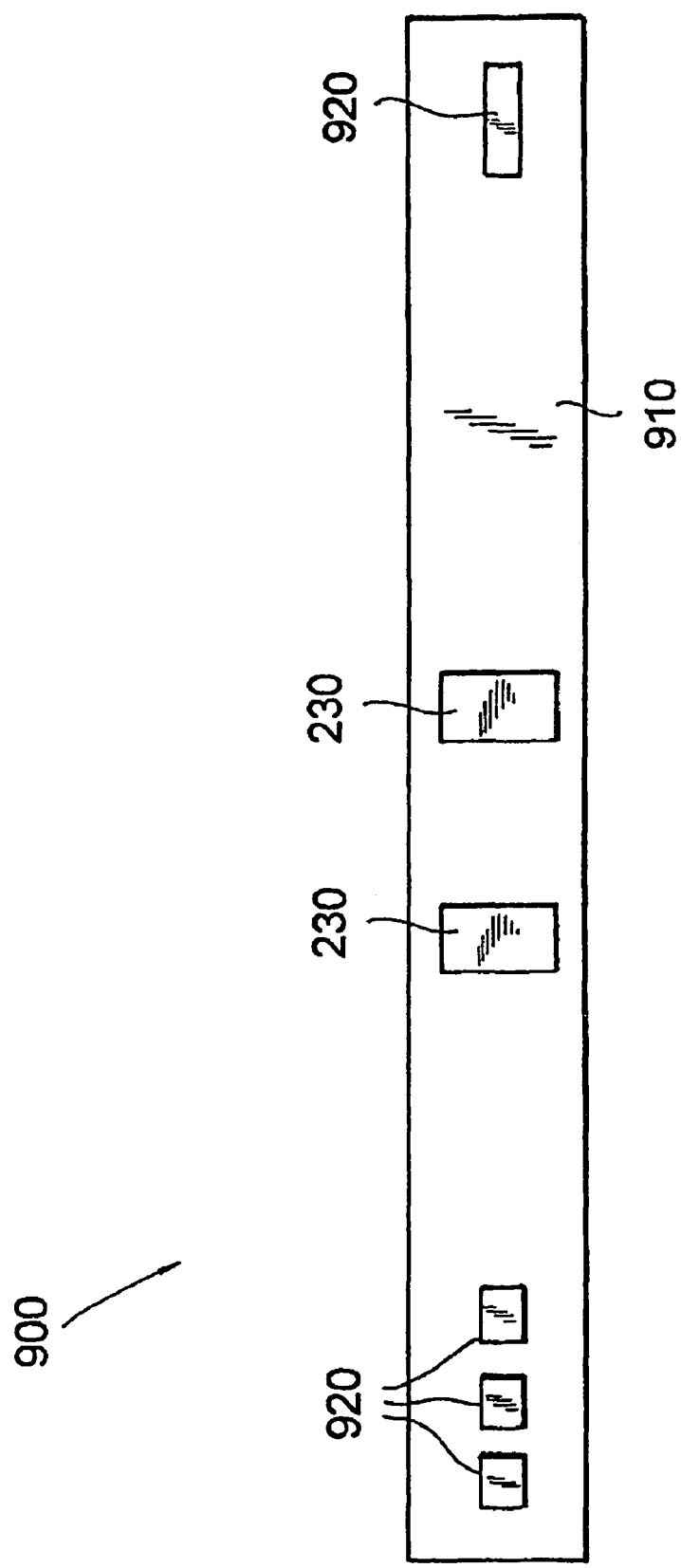
FIG. 20 is an elevational view of an unwrapped collar according to one exemplary embodiment for placement around a neck for treating a tumor or the like in this area when the collar is wrapped around the neck.

FIG. 20 illustrates yet another embodiment in which a high standing collar member 900 (or necklace type structure) can be used to treat thyroid, parathyroid, laryngeal lesions, etc.

FIG. 20 illustrates the collar member 900 in an unwrapped, substantially flat condition. In this embodiment, the insulated electrodes 230 are incorporated into a body 910 of the collar member 900 and are configured for placement against a neck area of the wearer. The insulated electrodes 230 are coupled to the generator 210 according to any of the manner described hereinbefore and it will be appreciated that the generator 210 can be disposed within the body 910 or it can be disposed in a location external to the body 910. The collar body 910 can be formed of any number of materials that are traditionally used to form collars 900 that are disposed around a person's neck. As such, the collar 900 preferably includes a means 920 for adjusting the collar 900 relative to the neck. For example, complementary fasteners (hook and loop fasteners, buttons, etc.) can be disposed on ends of the collar 900 to permit adjustment of the collar diameter.

Thus, the construction of the present devices are particularly well suited for applications where the devices are incorporated into articles of clothing to permit the patient to easily wear a traditional article of clothing while at the same time the patient undergoes treatment. In other words, an extra level of comfort can be provided to the patient and the effectiveness of the treatment can be increased by incorporating some or all of the device components into the article of clothing. The precise article of clothing that the components are incorporated into will obviously vary depending upon the target area of the living tissue where tumor, lesion or the like exists. For example, if the target area is in the testicle area of a male patient, then an article of clothing in the form of a sock-like structure or wrap can be provided and is configured to be worn around the testicle area of the patient in such a manner that the insulated electrodes thereof are positioned relative to the tumor such that the TC fields are directed at the target tissue. The precise nature or form of the article of clothing can vary greatly since the device components can be incorporated into most types of articles of clothing and therefore, can be used to treat any number of different areas of the patient's body where a condition may be present.

Figure 21:
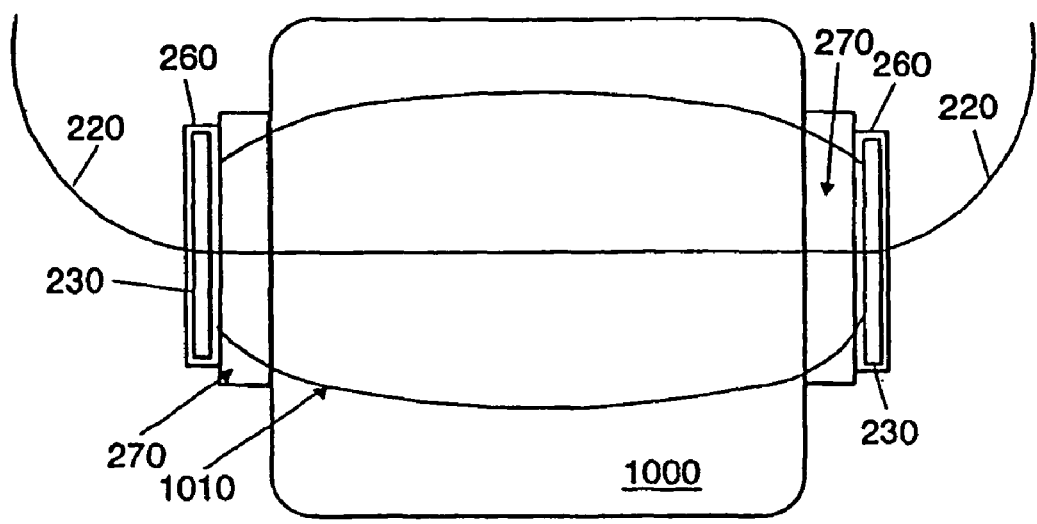
FIG. 21 is a cross-sectional view of two insulated electrodes with conductive gel members being arranged about a body, with the electric field lines being shown.
Figure 22:
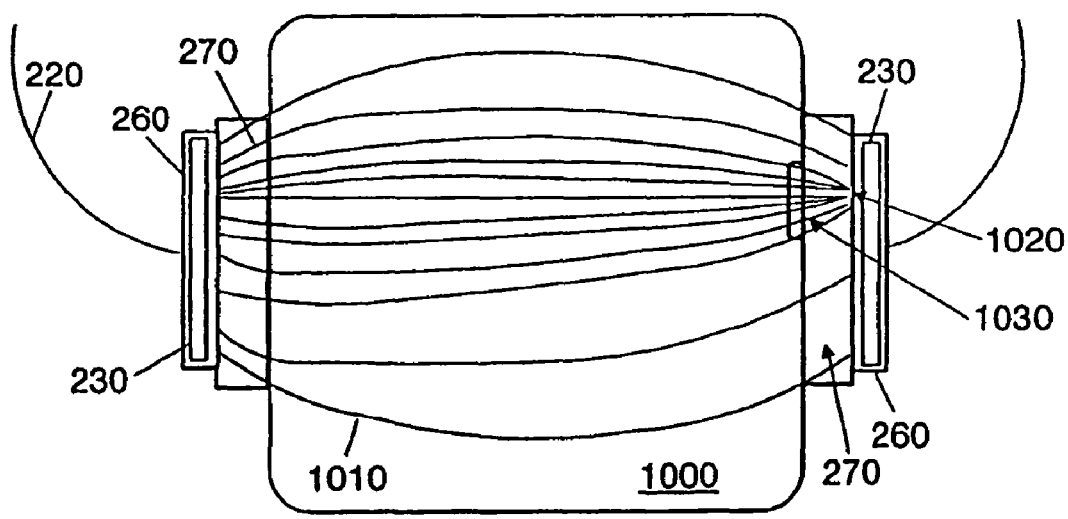
FIG. 22 is a cross-sectional view of the arrangement of FIG. 21 illustrating a point of insulation breakdown in one insulated electrode.

Now turning to FIGS. 21-22 in which another aspect of the present device is shown. In FIG. 21, a body 1000, such as any number of parts of a human or animal body, is illustrated. As in the previous embodiments, two or more insulated electrodes 230 are disposed in proximity to the body 1000 for treatment of a tumor or the like (not shown) using TC fields, as has been previously described in great detail in the above discussion of other embodiments. The insulated electrode 230 has a conductive component and has external insulation 260 that surrounds the conductive component thereof. Each insulated electrode 230 is preferably connected to a generator (not shown) by the lead 220. Between each insulated electrode 220 and the body 1000, a conductive filler material (e.g., conductive gel member 270) is disposed. The insulated electrodes 230 are spaced apart from one another and when the generator is actuated, the insulated electrodes 230 generate the TC fields that have been previously described in great detail. The lines of the electric field (TC field) are generally illustrated at 1010. As shown, the electric field lines 1010 extend between the insulated electrodes 230 and through the conductive gel member 270.

Over time or as a result of some type of event, the external insulation 260 of the insulated electrode 230 can begin to breakdown at any given location thereof. For purpose of illustration only, FIG. 22 illustrates that the external insulation 260 of one of the insulated electrodes 230 has experienced a breakdown 1020 at a face thereof which is adjacent the conductive gel member 270. It will be appreciated that the breakdown 1020 of the external insulation 260 results in the formation of a strong current flow-current density at this point (i.e., at the breakdown 1020). The increased current density is depicted by the increased number of electric field lines 1010 and the relative positioning and distance between adjacent electric field lines 1010. One of the side effects of the occurrence of breakdown 1020 is that current exists at this point which will generate heat and may burn the tissues/skin which have a resistance. In FIG. 22, an overheated area 1030 is illustrated and is a region or area of the tissues/skin where an increased current density exits due to the breakdown 1020 in the external insulation 260. A patient can experience discomfort and pain in this area 1030 due to the strong current that exists in the area and the increased heat and possible burning sensation that exist in area 1030.

Figure 23:
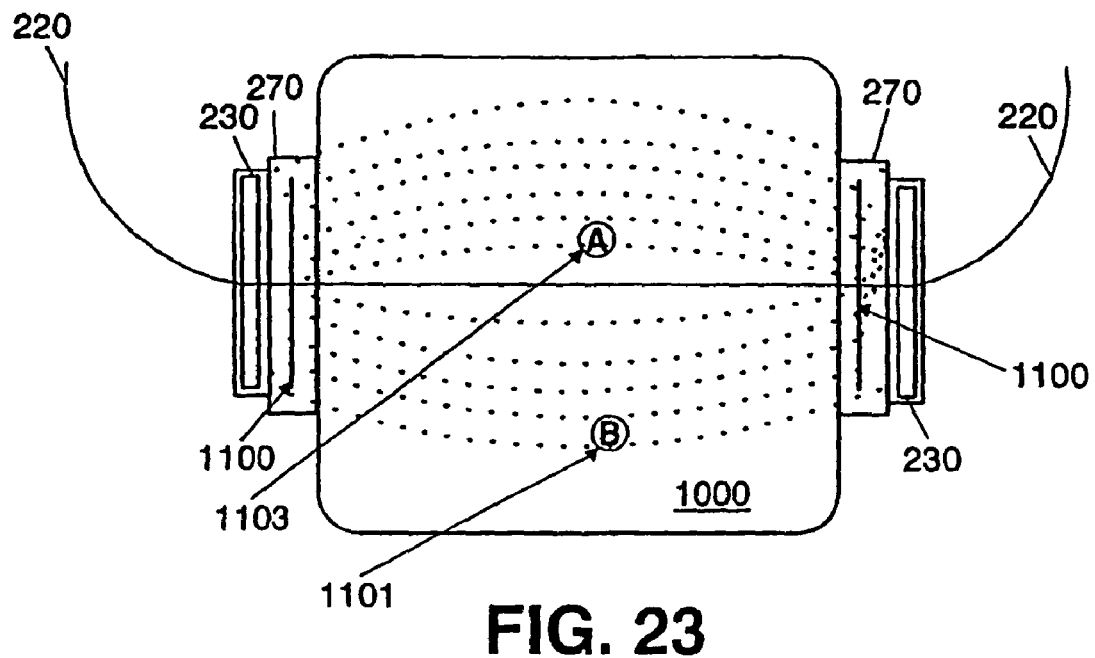
FIG. 23 is a cross-sectional view of an arrangement of at least two insulated electrodes with conductive gel members being arranged about a body for treatment of a tumor or the like, wherein each conductive gel member has a feature for minimizing the effects of an insulation breakdown in the insulated electrode.

FIG. 23 illustrates yet another embodiment in which a further application of the insulated electrodes 230 is shown. In this embodiment, the conductive gel member 270 that is disposed between the insulated electrode 230 and the body 1000 includes a conductor 1100 that is floating in that the gel material forming the member 270 completely surrounds the conductor 1100. In one exemplary embodiment, the conductor 1100 is a thin metal sheet plate that is disposed within the conductor 1100. As will be appreciated, if a conductor, such as the plate 1100, is placed in a homogeneous electric field, normal to the lines of the electric field, the conductor 1100 practically has no effect on the field (except that the two opposing faces of the conductor 1100 are equipotential and the corresponding equipotentials are slightly shifted). Conversely, if the conductor 1100 is disposed parallel to the electric field, there is a significant distortion of the electric field. The area in the immediate proximity of the conductor 1100 is not equipotential, in contrast to the situation where there is no conductor 1100 present. When the conductor 1100 is disposed within the gel member 270, the conductor 1100 will typically not effect the electric field (TC field) for the reasons discussed above, namely that the conductor 1100 is normal to the lines of the electric field.

If there is a breakdown of the external insulation 260 of the insulated electrode 230, there is a strong current flow-current density at the point of breakdown as previously discussed; however, the presence of the conductor 1100 causes the current to spread throughout the conductor 1100 and then exit from the whole surface of the conductor 1100 so that the current reaches the body 1000 with a current density that is neither high nor low. Thus, the current that reaches the skin will not cause discomfort to the patient even when there has been a breakdown in the insulation 260 of the insulated electrode 230. It is important that the conductor 1100 is not grounded as this would cause it to abolish the electric field beyond it. Thus, the conductor 1100 is "floating" within the gel member 270.

If the conductor 1100 is introduced into the body tissues 1000 and is not disposed parallel to the electric field, the conductor 100 will cause distortion of the electric field. The distortion can cause spreading of the lines of force (low field density-intensity) or concentration of the lines of field (higher density) of the electric field, according to the particular geometries of the insert and its surroundings, and thus, the conductor 1100 can exhibit, for example, a screening effect. Thus, for example, if the conductor 1100 completely encircles an organ 1101, the electric field in the organ itself will be zero since this type of arrangement is a Faraday cage. However, because it is impractical for a conductor to be disposed completely around an organ, a conductive net or similar structure can be used to cover, completely or partially, the organ, thereby resulting in the electric field in the organ itself being zero or about zero. For example, a net can be made of a number of conductive wires that are arranged relative to one another to form the net or a set of wires can be arranged to substantially encircle or otherwise cover the organ 1101. Conversely, an organ 1103 to be treated (the target organ) is not covered with a member having a Faraday cage effect but rather is disposed in the electric field 1010 (TC fields).

Figure 24:
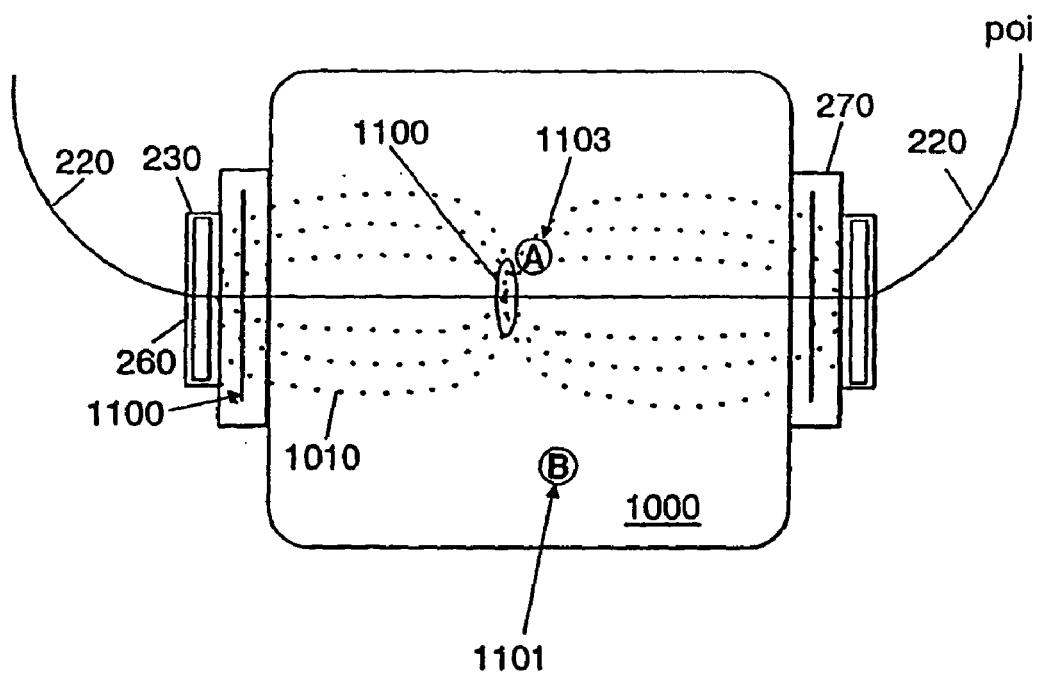
FIG. 24 is a cross-sectional view of another arrangement of at least two insulated electrodes with conductive gel members being arranged about a body for treatment of a tumor or the like, wherein a conductive member is disposed within the body near the tumor to create a region of increased field density.

FIG. 24 illustrates an embodiment where the conductor 1100 is disposed within the body (i.e., under the skin) and it is located near a target (e.g., a target organ). By placing the conductor 1100 near the target, high field density (of the TC fields) is realized at the target. At the same time, another nearby organ can be protected by disposing the above described protective conductive net or the like around this nearby organ so as to protect this organ from the fields. By positioning the conductor 1100 in close proximity to the target, a high field density condition can be provided near or at the target. In other words, the conductor 1100 permits the TC fields to be focused at a particular area (i.e., a target).

It will also be appreciated that in the embodiment of FIG. 24, the gel members 260 can each include a conductor as described with reference to FIG. 23. In such an arrangement, the conductor in the gel member 260 protects the skin surface (tissues) from any side effects that may be realized if a breakdown in the insulation of the insulated electrode 230 occurs. At the same time, the conductor 1100 creates a high field density near the target.

Figure 25:
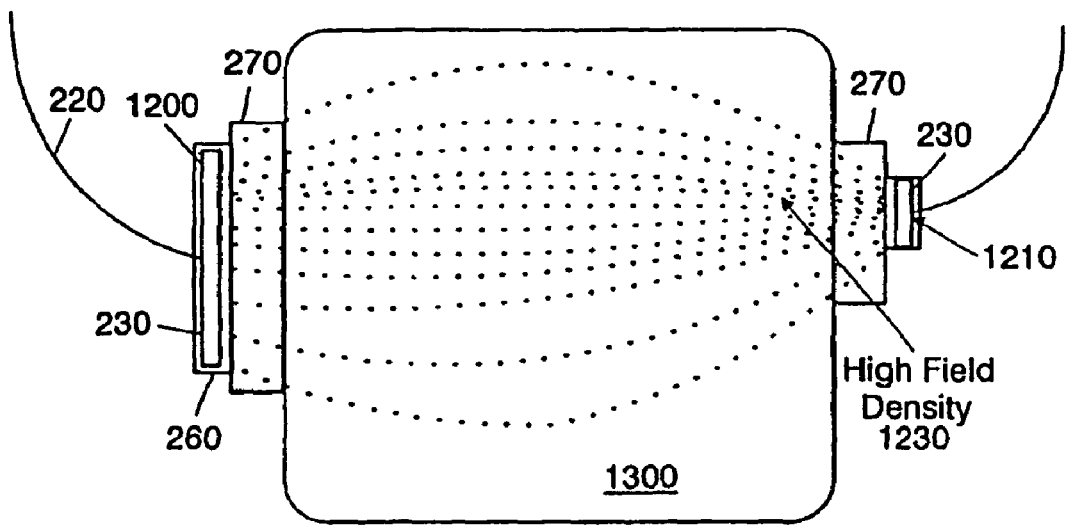
FIG. 25 is a cross-sectional view of an arrangement of two insulated electrodes of varying sizes disposed relative to a body.

There are a number of different ways to tailor the field density of the electric field by constructing the electrodes differently and/or by strategically placing the electrodes relative to one another. For example, in FIG. 25, a first insulated electrode 1200 and a second insulated electrode 1210 are provided and are disposed about a body 1300. Each insulated electrode includes a conductor that is preferably surrounded by an insulating material, thus the term "insulated electrode". Between each of the first and second electrodes 1200, 1210 and the body 1300, the conductive gel member 270 is provided. Electric field lines are generally indicated at 1220 for this type of arrangement. In this embodiment, the first insulated electrode 1200 has dimensions that are significantly greater than the dimensions of the second insulated electrode 1210 (the conductive gel member for the second insulated electrode 1210 will likewise be smaller).

By varying the dimensions of the insulated electrodes, the pattern of the electric field lines 1220 is varied. More specifically, the electric field tapers inwardly toward the second insulated electrode 1210 due to the smaller dimensions of the second insulated electrode 1210. An area of high field density, generally indicated at 1230, forms near the interface between the gel member 270 associated with the second insulated electrode 1210 and the skin surface. The various components of the system are manipulated so that the tumor within the skin or on the skin is within this high field density so that the area to be treated (the target) is exposed to electric field lines of a higher field density.

Figure 26:
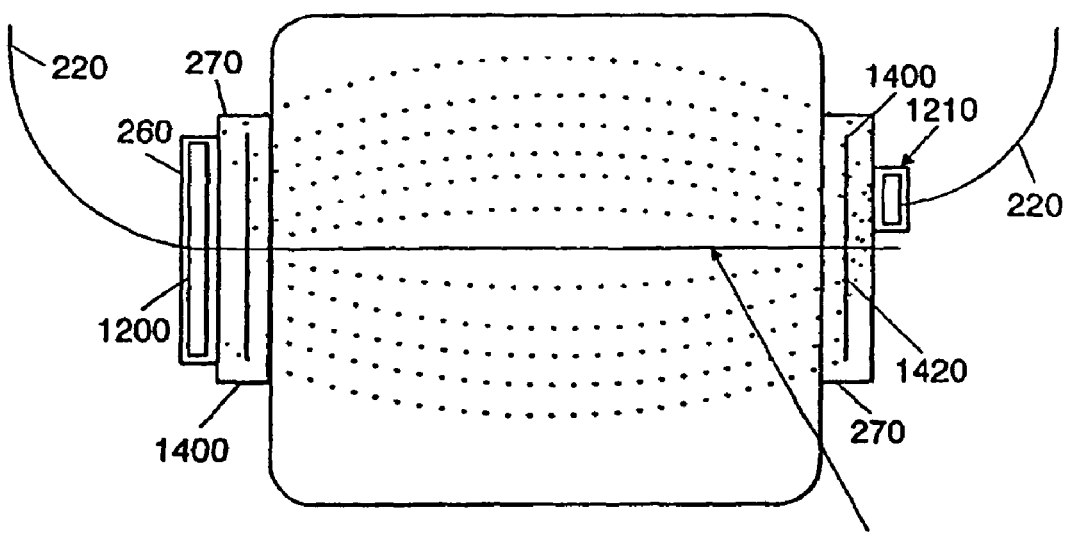
FIG. 26 is a cross-sectional view of an arrangement of at least two insulated electrodes with conductive gel members being arranged about a body for treatment of a tumor or the like, wherein each conductive gel member has a feature for minimizing the effects of an insulation breakdown in the insulated electrode.

FIG. 26 also illustrates a tapering TC field when a conductor 1400 (e.g., a conductive plate) is disposed in each of the conductive gel members 270. In this embodiment, the size of the gel members 270 and the size of the conductors 1400 are the same or about the same despite the differences in the sizes of the insulated electrodes 1200, 1210. The conductors 1400 again can be characterized as "floating plates" since each conductor 1400 is surrounded by the material that forms the gel member 270. As shown in FIG. 26, the placement of one conductor 1400 near the insulated electrode 1210 that is smaller than the other insulated electrode 1200 and is also smaller than the conductor 1400 itself and the other insulated electrode 1200 is disposed at a distance therefrom, the one conductor 1400 causes a decrease in the field density in the tissues disposed between the one conductor 1400 and the other insulated electrode 1200. The decrease in the field density is generally indicated at 1410. At the same time, a very inhomogeneous tapering field, generally indicated at 1420, changing from very low density to very high density is formed between the one conductor 1400 and the insulated electrode 1210. One benefit of this exemplary configuration is that it permits the size of the insulated electrode to be reduced without causing an increase in the nearby field density. This can be important since electrodes that having very high dielectric constant insulation can be very expensive. Some insulated electrodes, for example, can cost $500.00 or more; and further, the price is sensitive to the particular area of treatment. Thus, a reduction in the size of the insulated electrodes directly leads to a reduction in cost.

As used herein, the term "tumor" refers to a malignant tissue comprising transformed cells that grow uncontrollably. Tumors include leukemias, lymphomas, myelomas, plasmacytomas, and the like; and solid tumors. Examples of solid tumors that can be treated according to the invention include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. Because each of these tumors undergoes rapid growth, any one can be treated in accordance with the invention. The invention is particularly advantageous for treating brain tumors, which are difficult to treat with surgery and radiation, and often inaccessible to chemotherapy or gene therapies. In addition, the present invention is suitable for use in treating skin and breast tumors because of the ease of localized treatment provided by the present invention.

In addition, the present invention can control uncontrolled growth associated with non-malignant or pre-malignant conditions, and other disorders involving inappropriate cell or tissue growth by application of an electric field in accordance with the invention to the tissue undergoing inappropriate growth. For example, it is contemplated that the invention is useful for the treatment of arteriovenous (AV) malformations, particularly in intracranial sites. The invention may also be used to treat psoriasis, a dermatologic condition that is characterized by inflammation and vascular proliferation; and benign prostatic hypertrophy, a condition associated with inflammation and possibly vascular proliferation. Treatment of other hyperproliferative disorders is also contemplated.

Furthermore, undesirable fibroblast and endothelial cell proliferation associated with wound healing, leading to scar and keloid formation after surgery or injury, and restenosis after angioplasty or placement of coronary stents can be inhibited by application of an electric field in accordance with the present invention. The non-invasive nature of this invention makes it particularly desirable for these types of conditions, particularly to prevent development of internal scars and adhesions, or to inhibit restenosis of coronary, carotid, and other important arteries.

In addition to treating tumors that have already been detected, the above-described embodiments may also be used prophylactically to prevent tumors from ever reaching a detectable size in the first place. For example, the bra embodiment described above in connection with FIGS. 17 and 18 may be worn by a woman for an 8 hour session every day for a week, with the week-long course of treatment being repeated every few months to kill any cells that have become cancerous and started to proliferate. This mode of usage is particularly appropriate for people who are at high risk for a particular type of cancer (e.g., women with a strong history of breast cancer in their families, or people who have survived a bout of cancer and are at risk of a relapse). The course of prophylactic treatment may be tailored based on the type of cancer being targeted and/or to suit the convenience of the patient. For example, undergoing a four 16 hour sessions during the week of treatment may be more convenient for some patients than seven 8 hour session, and may be equally effective.

Thus, the present invention provides an effective, simple method of selectively destroying dividing cells, e.g., tumor cells and parasitic organisms, while non-dividing cells or organisms are left affected by application of the method on living tissue containing both types of cells or organisms. Thus, unlike many of the conventional methods, the present invention does not damage the normal cells or organisms. In addition, the present invention does not discriminate based upon cell type (e.g., cells having differing sizes) and therefore may be used to treat any number of types of sizes having a wide spectrum of characteristics, including varying dimensions.

While the invention has been particularly shown and described with reference to preferred embodiments thereof, it will be understood by those skilled in the art that various changes in form and details can be made without departing from the spirit and scope of the invention.

What is claimed is:

1. An apparatus for selectively destroying dividing cells in living tissue, the dividing cells having polarizable or polar intracellular members, the apparatus comprising:
   a first electrode having a first surface configured for placement against the living tissue, the first electrode having a first conductor that is electrically insulated from the first surface;
   a second electrode having a second surface configured for placement against the living tissue, the second electrode having a second conductor that is electrically insulated from the second surface; and
   an alternating voltage source for applying an alternating electric potential across the first and second conductors so that an electric field is produced in the living tissue, wherein passage of the electric field through the dividing cells in late anaphase or telophase transforms the electric field into a non-homogenous electric field that produces an increased density electric field in a region of a cleavage furrow of the dividing cells, and wherein the electric field has amplitude and frequency characteristics such that long-term application of the electric field causes the destruction of cells as they divide, but wherein the electric field is sufficiently small so that during long-term application of the electric field, the destruction of the dividing cells is not caused by heat.

2. The apparatus of claim 1, wherein the frequency of the electric field is such that the non-homogeneous electric field produced in the dividing cells defines electric field lines which generally converge at a region of the cleavage furrow, thereby defining the increased density electric field, resulting in destruction of the dividing cells as a result of the polarizable intracellular members movement toward the furrow.

3. The apparatus of claim 1, wherein the first conductor is electrically insulated from the first surface by a dielectric member.

4. The apparatus of claim 3, wherein the second conductor is electrically insulated from the second surface by a dielectric member.

5. The apparatus of claim 4, wherein each of the first and second dielectric members comprises a layer of titanium dioxide.

6. The apparatus of claim 4, wherein each of the first and second dielectric members comprises a dielectric coating having a thickness between about 5 microns to about 50 microns.

7. The apparatus of claim 6, further including: a thin conducting coating disposed on the dielectric coating for contacting the tissue.

8. The apparatus of claim 1, wherein the alternating electric potential has a frequency of between about 50 KHz to about 500 KHz.

9. The apparatus of claim 1, wherein the alternating electric potential has a frequency of between about 100 KHz to about 300 KHz.

10. The apparatus of claim 9, wherein the voltage waveform is selected so that an electric field intensity in tissue to be treated is between about 0.1 V/cm to about 10 V/cm.

11. The apparatus of claim 9, wherein the voltage waveform is selected so that an electric field intensity in tissue to be treated is between about 1 V/cm to about 5 V/cm.

12. A method for selectively destroying dividing cells in living tissue, the dividing cells having polarizable intracellular members, the method comprising the steps of:
   positioning first and second electrodes in relation to the living tissue, each of the electrodes having a surface configured for placement against the living tissue and a conductor that is electrically insulated from the surface;
   applying an alternating electric potential between the first and second conductors so that the living tissue is subjected to an alternating electric field,
   wherein passage of the electric field through the dividing cells in late anaphase or telophase transforms the electric field into a non-homogeneous electric field that produces an increased density electric field in a region of a cleavage furrow of the dividing cells, and wherein the electric field has amplitude and frequency characteristics such that long-term application of the electric field causes the destruction of cells as they divide, but wherein the electric field is sufficiently small so that during long-term application of the electric field, the destruction of the dividing cells is not caused by heat.

13. The method of claim 12, wherein the frequency of the electric field is such that the non-homogeneous electric field produced in the dividing cells defines electric field lines which generally converge at a region of the cleavage furrow, thereby defining the increased density electric field, resulting in destruction of the dividing cells as a result of the polarizable intracellular members movement toward the furrow.

14. The method of claim 12, wherein positioning the first and second electrodes comprises: positioning the surfaces in contact with the living tissue.

15. The method of claim 12, wherein positioning the first and second electrodes comprises: positioning the surfaces in contact with the living tissue with a conductive gel disposed between each of the surfaces and the living tissue.

16. The method of claim 12, wherein the alternating electric field has a frequency between about 50 KHz and about 500 KHz.

17. The method of claim 12, wherein the alternating electric field has a frequency between about 100 KHz and about 300 KHz.

18. The method of claim 17, wherein the electric field intensity in the living tissue is between about 1 V/cm to about 5 V/cm.

19. The method of claim 12, further comprising the step of: rotating the electric field with respect to the living tissue.

20. An apparatus for selectively destroying dividing cells that are in a localized area of living tissue, the dividing cells having polarizable intracellular members, the apparatus comprising:

at least two electrodes, each electrode having an associated conductor and a dielectric material configured for placement against living tissue that insulates the conductor from the living tissue; and an electric field source for applying an alternating electric potential across the conductors such that a resulting electric field in the dividing cells is transformed into a non-homogenous electric field that produces an increased density electric field in a region of the dividing cells, the non-homogenous electric field being of sufficient intensity to cause the intracellular members to be drawn to the region where the electric field has increased density to cause a pressure increase in this region which causes a structural breakdown of the dividing cells wherein the electric field is sufficiently small such that the structural breakdown of the dividing cells is not caused by heat.

* * * * *